(12) United States Patent
Namati et al.

(10) Patent No.: US 9,706,926 B2
(45) Date of Patent: Jul. 18, 2017

(54) ANGULAR IMAGE MANIPULATION

(71) Applicants: Eman Namati, Belmont, MA (US); Paul Neumann, Boston, MA (US)

(72) Inventors: Eman Namati, Belmont, MA (US); Paul Neumann, Boston, MA (US)

(73) Assignee: NinePointMedical, Cambridge, MA (US)

(*) Notice: Subject to any disclaimer, the term of this patent is extended or adjusted under 35 U.S.C. 154(b) by 139 days.

(21) Appl. No.: 14/279,622

(22) Filed: May 16, 2014

(65) Prior Publication Data

US 2014/0343411 A1 Nov. 20, 2014

(51) Int. Cl.
*G06K 9/00* (2006.01)
*A61B 5/00* (2006.01)
*A61B 5/06* (2006.01)
*G01B 9/02* (2006.01)
*A61B 5/05* (2006.01)

(52) U.S. Cl.
CPC .......... *A61B 5/0073* (2013.01); *A61B 5/0066* (2013.01); *A61B 5/061* (2013.01); *A61B 5/72* (2013.01); *A61B 5/7257* (2013.01); *G01B 9/02058* (2013.01); *G01B 9/02083* (2013.01); *G01B 9/02089* (2013.01); *G01B 9/02091* (2013.01); *A61B 2576/00* (2013.01); *G01B 2290/70* (2013.01)

(58) Field of Classification Search
CPC ............... G06K 9/00; A61B 5/00; G01B 9/00
USPC ............ 382/128–134; 378/4, 8, 21–27, 901; 600/407, 410, 411, 425, 427
See application file for complete search history.

(56) References Cited

U.S. PATENT DOCUMENTS

| | | | |
|---|---|---|---|
| 6,628,982 B1* | 9/2003 | Thomas | A61B 90/39 600/431 |
| 7,333,648 B2* | 2/2008 | Edic | G06T 7/0012 382/131 |
| 8,123,679 B2* | 2/2012 | Xie | A61B 1/00154 600/117 |
| 2007/0106155 A1 | 5/2007 | Goodnow et al. | |
| 2009/0018393 A1 | 1/2009 | Dick et al. | |
| 2012/0108969 A1 | 5/2012 | Cai | |
| 2013/0100455 A1 | 4/2013 | Tearney et al. | |
| 2013/0107274 A1 | 5/2013 | Vertikov et al. | |

OTHER PUBLICATIONS

International Search Report and Written Opinion mailed Aug. 20, 2014,for International Application No. PCT/ US2014/038327 filed May 16, 2014. (9 pages).

* cited by examiner

*Primary Examiner* — Abolfazl Tabatabai

(57) ABSTRACT

The present disclosure provides an OCT imaging system having a variety of advantages. In particular, the OCT system of the present disclosure may provide a more intuitive interface, more efficient usage of controls, and a greater ability to view OCT imaging data.

16 Claims, 21 Drawing Sheets

OCT System
100

ANGULAR IMAGE MANIPULATION

CROSS REFERENCE TO RELATED APPLICATIONS

This application claims the benefit of U.S. Provisional Application Ser. No. 61/824,688 filed May 17, 2013, entitled "Enhanced Frequency-Domain Optical Coherence Tomography Systems," which application is incorporated herein by reference in its entirety.

TECHNICAL FIELD

The present disclosure relates to optical imaging systems, in particular optical imaging systems utilizing frequency-domain interferometry.

BACKGROUND

Frequency-domain (or "swept-source") optical coherence tomography (OCT) systems are powerful tools that provide non-invasive, high-resolution images of biological samples at higher acquisition speeds and lower signal-to-noise ratios than time-domain OCT systems. FIG. 1 illustrates an exemplary frequency-domain OCT system 100 at a high level. As shown, the exemplary OCT system includes a wavelength-swept laser source 95 (also referred to herein as a frequency swept source) that provides a laser output spectrum composed of single or multiple longitudinal modes to an input of a coupler 72. The coupler 72 divides the signal fed thereto into the reference arm 80 that terminates in the reference mirror 82 and the sample arm 84 that terminates in the sample 86. The optical signals reflect from the reference mirror 82 and the sample 86 to provide, via the coupler 72, a spectrum of signals that are detected by a photo-detector 88.

Despite the many advantages of frequency-domain OCT, conventional implementations can be difficult to set up and optimize. Additionally, conventional implementations can have differences in measured properties and dimensions from system-to-system. It is with respect to this, that the present disclosure is provided.

DESCRIPTION OF EMBODIMENTS

Figure 1:
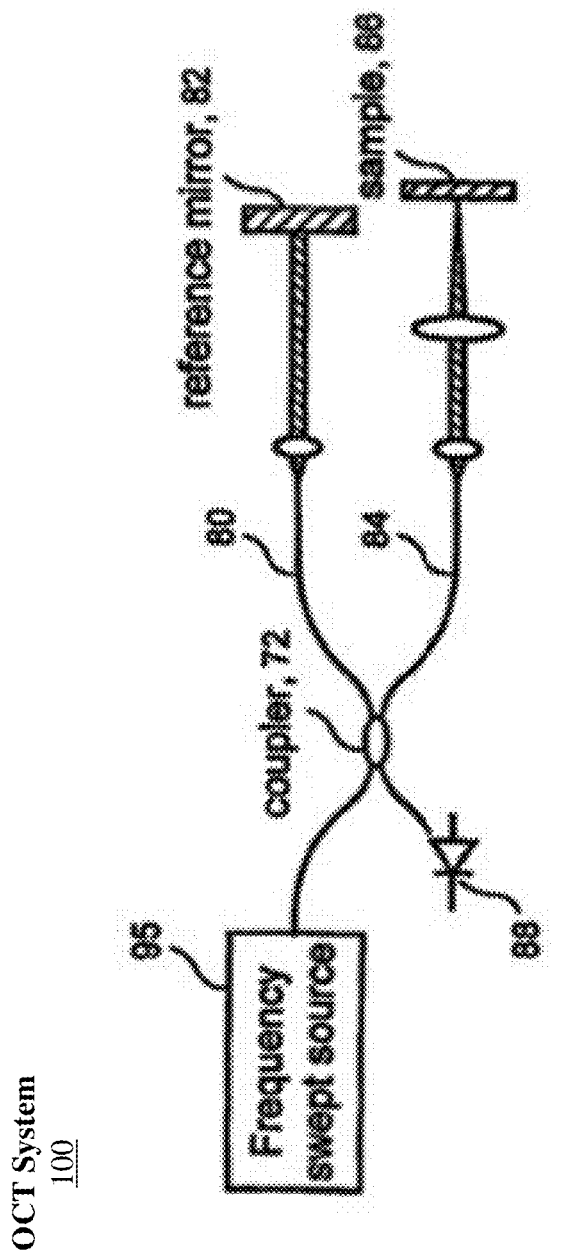
FIG. 1 illustrates a block diagram of a conventional frequency-domain OCT system.
Figure 2:
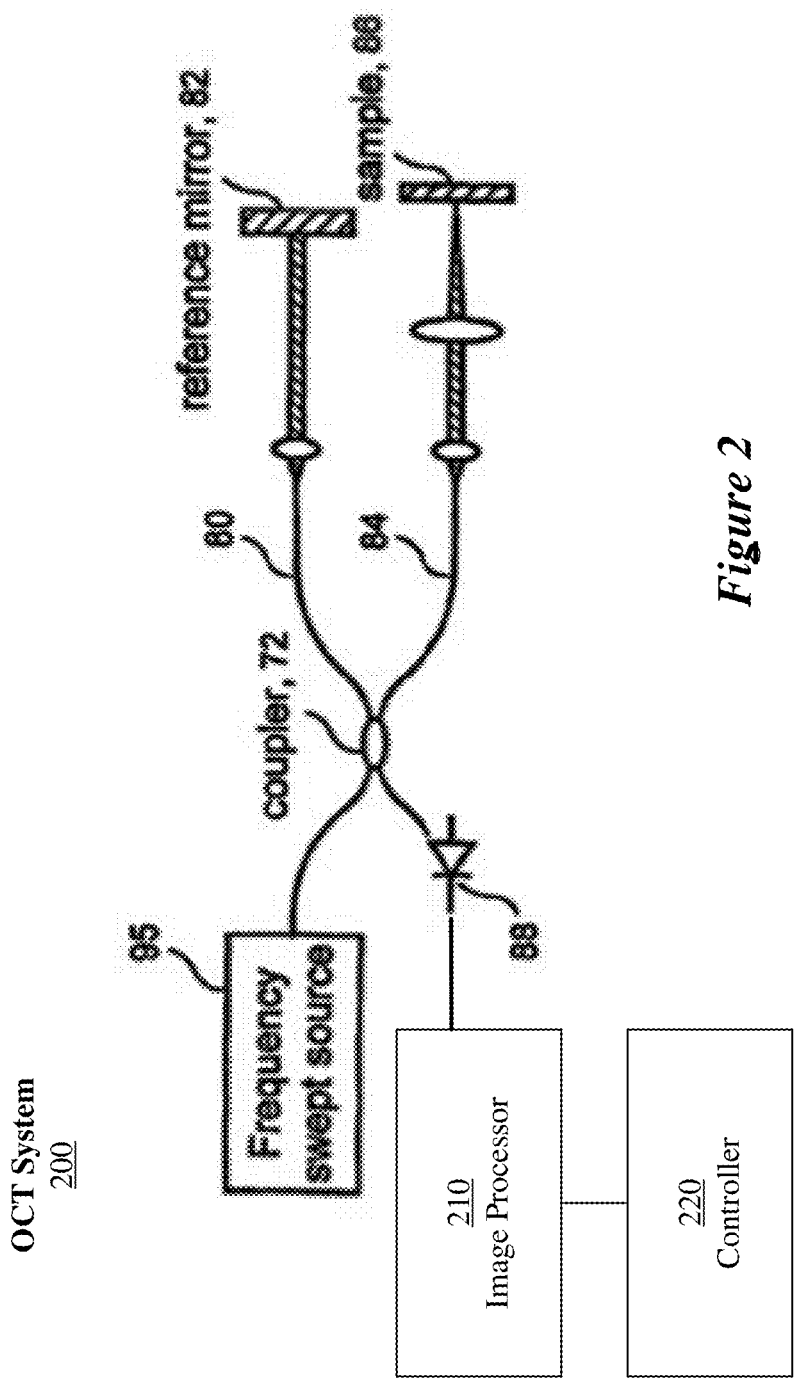
FIG. 2 illustrates a block diagram of a frequency-domain OCT system arranged according to examples of the present disclosure.

In general, the present disclosure provides a variety of apparatuses and methods related to frequency-domain OCT systems. FIG. 2 shows a high level diagram of a frequency-domain OCT system 200, which may be implemented according to various embodiments of the present disclosure. The system 200 includes a wavelength-swept light source 95 that provides a light having an output spectrum composed of single or multiple longitudinal modes. The source 95 provides the light to an input of a coupler 72. The coupler 72 divides the signal fed thereto into a reference arm 80 and a sample arm 84. The reference arm 80 terminates in the reference mirror 82, also referred to as a reference plane. The sample arm terminates in a sample 86. Optical images reflected from the sample 86 and the reference mirror 82 are received by a photodetector 88 and processed by a signal processor 210.

Additionally, the system 200 includes a controller 220. In general the signal processor 210 may be configured to implement various image processing operations on the images acquired by the system 200 while the controller 220 may be configured to control various aspects of the system 200. This will be described in greater detail below with reference to the example embodiments. It is important to note, that the controller 220 may be operably connected to various components within the system 200. However, these connections are not shown in FIG. 2 for clarity of presentation.

The signal processor 210 may be realized as software, hardware, or some combination thereof. The processor may also include a main memory unit for storing programs and/or data relating to the methods described herein. The memory may include random access memory (RAM), read only memory (ROM), and/or FLASH memory residing on commonly available hardware such as one or more ASICs, FPGAs, electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, or other storage devices.

For embodiments in which the functions of the processor are provided by software, the program may be written in any one of a number of high-level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

Additionally, the controller 220 may be realized as software, hardware, or some combination thereof. The processor may also include a main memory unit for storing programs and/or data relating to the methods described herein. The memory may include random access memory (RAM), read only memory (ROM), and/or FLASH memory residing on commonly available hardware such as one or more ASICs, FPGAs, electrically erasable programmable read-only memories (EEPROM), programmable read-only memories (PROM), programmable logic devices (PLD), or read-only memory devices (ROM). In some embodiments, the programs may be provided using external RAM and/or ROM such as optical disks, magnetic disks, or other storage devices.

For embodiments in which the functions of the processor are provided by software, the program may be written in any one of a number of high-level languages such as FORTRAN, PASCAL, JAVA, C, C++, C#, LISP, PERL, BASIC or any suitable programming language. Additionally, the software can be implemented in an assembly language and/or machine language directed to the microprocessor resident on a target device.

Other examples and aspects of the OCT system 200 are described in greater detail in U.S. Pat. No. 7,733,497 and U.S. patent application Ser. No. 13/412,787, the disclosures of which are both incorporated by reference herein in their entirety.

It is noted, that although various examples described herein reference the OCT system 200, this is merely done for convenience and clarity and is not intended to be limiting.

A. Automatic Path-Length Tuning

Some examples of the present disclosure provide for automatic tuning of the optical path length of the OCT system. As will be appreciated, in catheter-based OCT, catheters (i.e., the portion of the sample arm 84 that is typically introduced into the patient for imaging) generally have slightly different optical fiber lengths. This slight difference in optical fiber lengths results in differences in the optical path length between different catheters, even when used in the same OCT system. As OCT relies on optical path length measurements to generate images, these differences are conventionally compensated for individually, catheter-by-catheter.

Embodiments of the present disclosure automatically align the reference mirror 82 using the positions of known reflections from the catheter detected in the OCT images. In some examples, the reflections are due to different surfaces in the imaging catheter, including the optical probe components and/or the plastic lumen. These reflections give rise to fixed patterns in the OCT images; the positions of which may be determined using image processing techniques.

It is noted, that the present disclosure may be implemented to utilize the inherent structure of the catheter and may not require intentional addition of reference reflectors to the catheter. Moreover, embodiments may not require any additional hardware modifications to the system such as an additional interferometer.

Figure 3A:
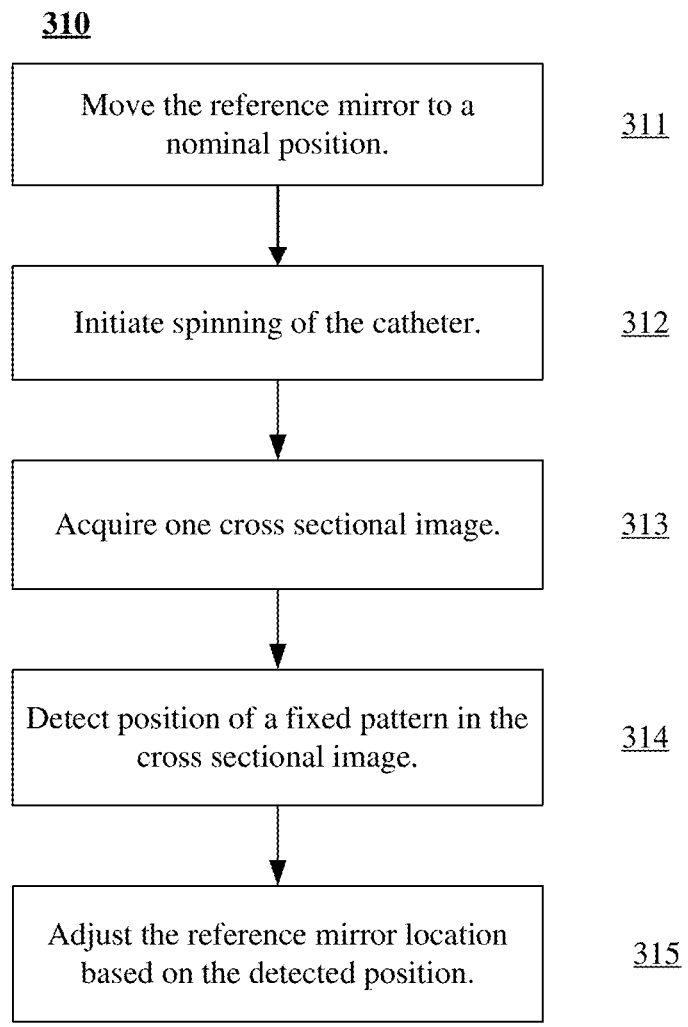
FIGS. 3A-3C illustrate logic flows for methods of tuning the optical path length according to examples of the present disclosure.
Figure 3B:
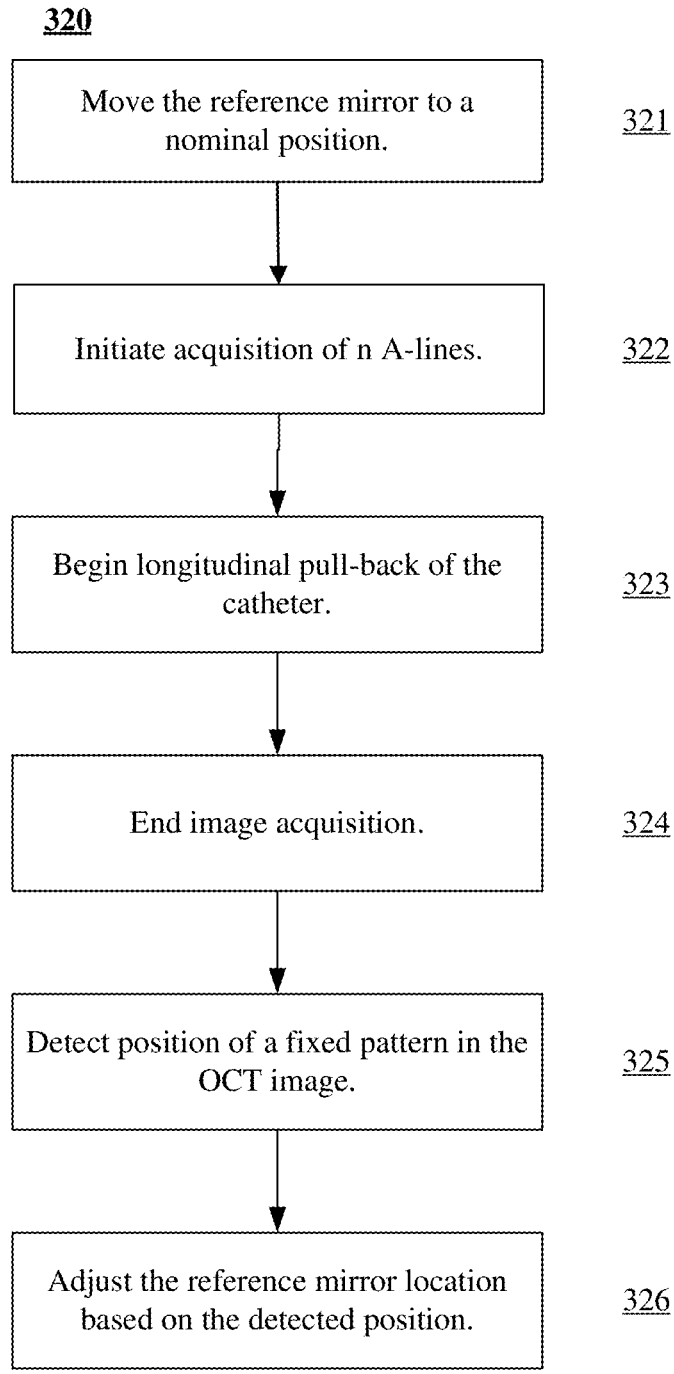
Figure 3C:
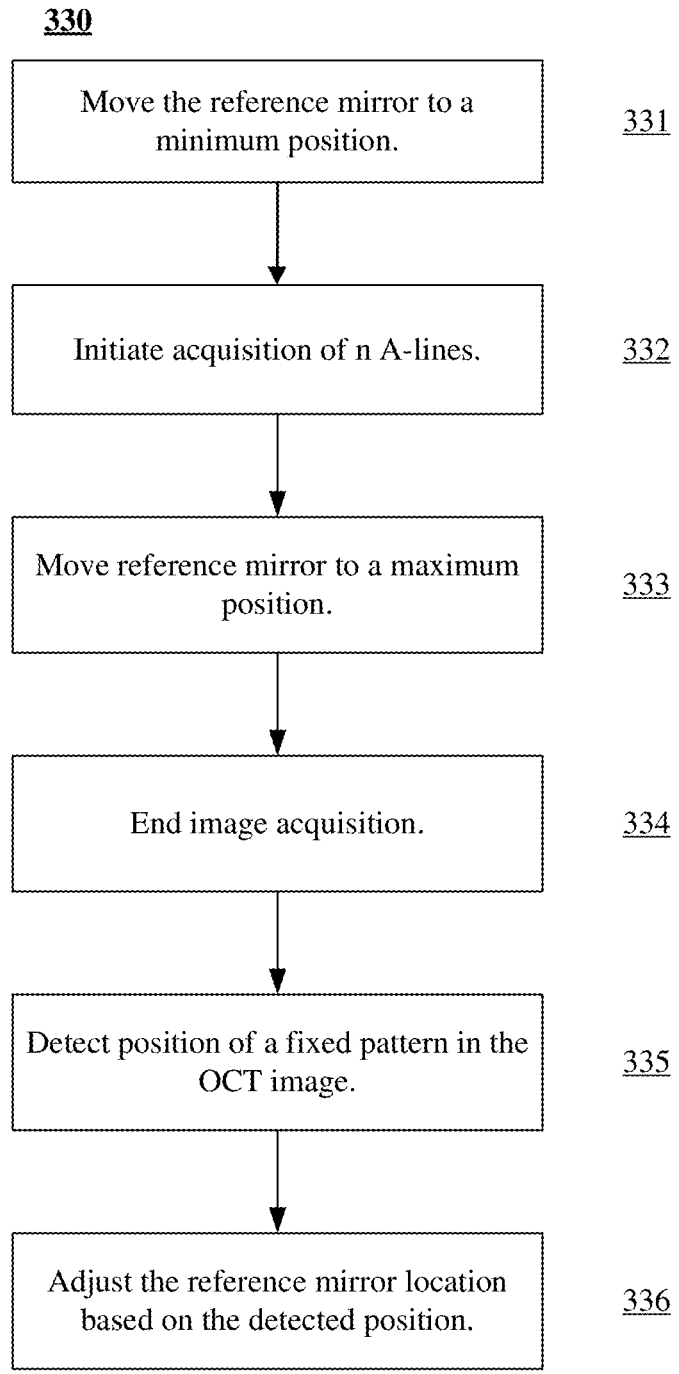

FIGS. 3A-3C illustrate example logic flows for methods of automatically "tuning" the optical path lengths of the OCT system. In general, the methods shown in these figures acquire OCT image data, for example following the connection of a new catheter to an OCT system. The signal processor 210 may be configured to apply image-processing techniques to the acquired images and to detect the position of a fixed pattern signal corresponding to a reflection from the distal end of the catheter.

The controller 220 may be configured to move the reference arm 80 and/or mirror 82 based on the detected position of the fixed pattern signals.

Turning more specifically to FIG. 3A, a method 310 for automatically tuning the optical path length in an OCT system is shown. The method 310 may include blocks 311-315. At block 311, the controller 220 may move the reference mirror 82 to a nominal position. At blocks 312 and 313, the catheter may be rotated to acquire (or collect) a single cross-sectional image when the reference mirror is at the nominal position.

At block 314, the signal processor 210 detects the location of a fixed pattern. At block 315, the controller 220 moves the reference mirror 82 to compensate for any slight variation in the optical path length from the nominal optical path length. It is noted that the method 310 assumes that the fixed pattern will be within the field-or-view of the OCT image when the reference mirror 82 is at the nominal position.

Turning more specifically to FIG. 3B, another method 320 for automatically tuning the optical path length in an OCT system is shown. The method 320 may include blocks 321-326. At block 321, the controller 220 may move the reference mirror 82 to a nominal position. At block 322, OCT image acquisition may be initiated for a fixed number (e.g., "n") OCT A-lines. At block 323, the controller 220 may pull the catheter back longitudinally during the acquisition of the OCT A-lines, until block 324, when acquisition of the n OCT A-lines is completed. At block 325, the signal processor 210 detects the location of a fixed pattern in the OCT image. At block 326, the controller 220 moves the reference mirror 82 to compensate for any slight variation in the optical path length from the nominal optical path length based on the position of the detected pattern.

An advantage to the methods 310 and 320 is that movement of the catheter will not change the characteristics of the image artifacts while the fixed pattern will remain substantially constant. This allows the fixed pattern feature in the images to be enhanced by averaging the OCT data.

Turning more specifically to FIG. 3C, another method 330 for automatically tuning the optical path length in an OCT system is shown. The method 330 may include blocks 331-336. At block 331, the controller 220 may move the reference mirror 82 to a minimum position. At block 332, OCT image acquisition may be initiated for a fixed number (e.g., "n") OCT A-lines. At block 333, the controller 220 may begin moving the reference mirror 82 to a maximum position while the n OCT A-lines are being acquired, until block 334, when acquisition of the n OCT A-lines is completed. At block 335, the signal processor 210 detects the location of a fixed pattern in the OCT image. At block 336, the controller 220 moves the reference mirror 82 to compensate for any slight variation in the optical path length from the nominal optical path length based on the position of the detected pattern. It is noted, that the method 330 does not require an initial nominal position of the reference mirror 82 to be set.

As described, the method 310, 320, and 330 implement image processing to detect the position of the fixed pattern in the OCT image. In particular, the signal processor 210 may implement one or more image processing algorithms to detect the position of the fixed pattern in the OCT image.

For example, the signal processor 210 may determine the distance between two reflections from the catheter sheath's inner and outer lumen. In some examples, the signal processor 210 may determine the distance between the catheter sheath reflection and the reflection from the optical probe's prism. In some examples, the signal processor 210 may determine the intensity of the reflections, either absolute or relative. In some examples, the signal processor 210 may determine the movement of the reflections in response to either spinning of the catheter or movement of the reference arm mirror. In some examples, the signal processor 210 may determine the texture of the reflection (i.e., speckle patterns). In some examples, the signal processor 210 may determine the presence of certain image artifacts that are due to the reflections. In some example, the signal processor 210 may determine the relationships between reflections with aliased reflections traveling in the same or opposite directions.

Figure 4B:
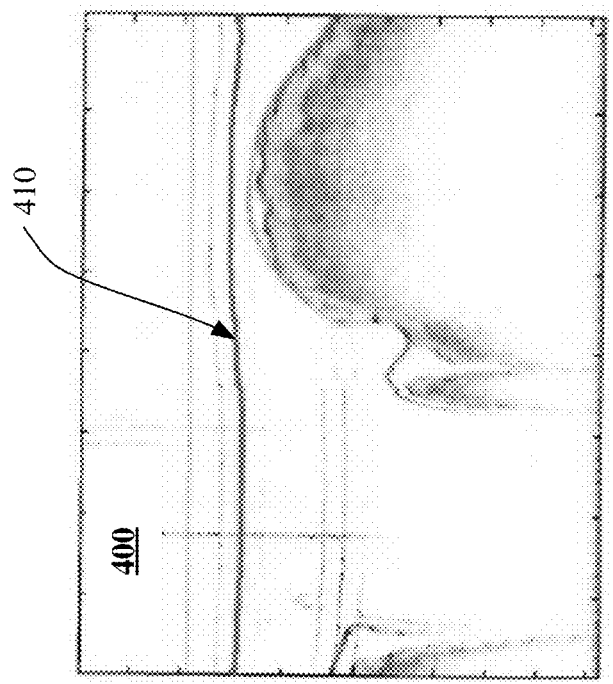
FIGS. 4A-4B illustrate examples of images acquired using an OCT system.
Figure 4A:
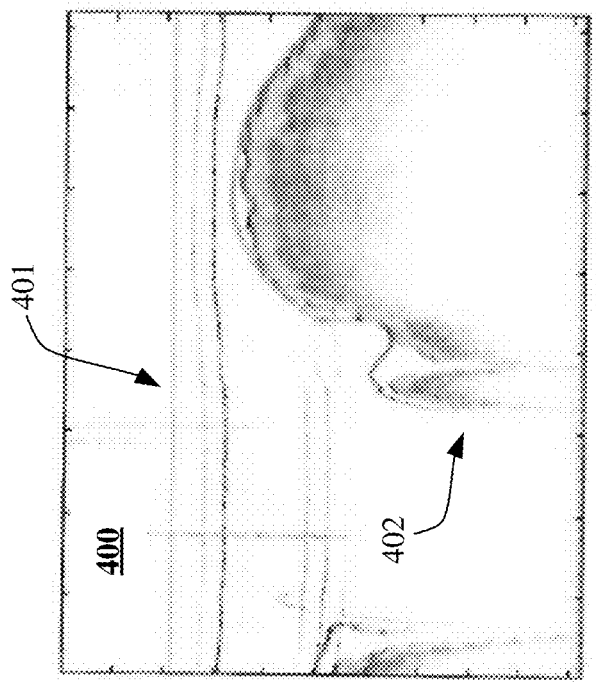

FIGS. 4A-4B illustrate an example of an image acquired while spinning the catheter. In particular, FIG. 4A depicts an OCT image 400 containing fixed pattern lines 401 as well as other image features 402. FIG. 4B depicts the OCT image 400, with an automatically detected catheter inner lumen reflection 410 (thick line). The signal processor 210 can automatically detect the reflection 410, for example, by applying the example image processing techniques described herein.

B. Interpolation-Based Digital Scale Adjustment

Some examples of the present disclosure provide for maintaining consistent dimensions of the OCT images. As will be appreciated, in swept-source OCT imaging systems, it may be challenging to maintain a fixed image dimension across different systems due to variability in the characteristics of the swept-source lasers (e.g., the swept-source laser 95) used to drive each system. For example, differences in the optical bandwidth as well as the duty cycle of the lasers may result in different spatial dimensions along the axial dimension of the images. However, it is advantageous to maintain constant image dimensions to facilitate comparing OCT images acquired using different systems.

In conventional system, the most common method for setting the axial range for an OCT system is to change the analog-to-digital converter (ADC) sample rate. However, the clock generators that are used for high speed ADCs typically do not have the ability to fine-tune the sample rate. More specifically, the sample rate can generally only be adjusted in large jumps. This lack of fine control over the sample rate limits the accuracy by which changing the sample rate may adjust the axial dimension.

Embodiments of the present disclosure utilize techniques for varying the image reconstruction parameters in OCT, in order to change the axial dimension of the images. In general, the axial dimensions of a system are measured using standard acquisition parameters and adjustments are made to achieve a desired axial range. Adjustment of the axial range may include, or consist essentially of, changing the effective sample rate of the raw acquired data by changing the interpolation parameters. Interpolation is a standard step in the OCT image reconstruction process. By introducing up sampling or down sampling into the interpolation, the effective sample rate and thus the digital range may be adjusted.

Figure 5:
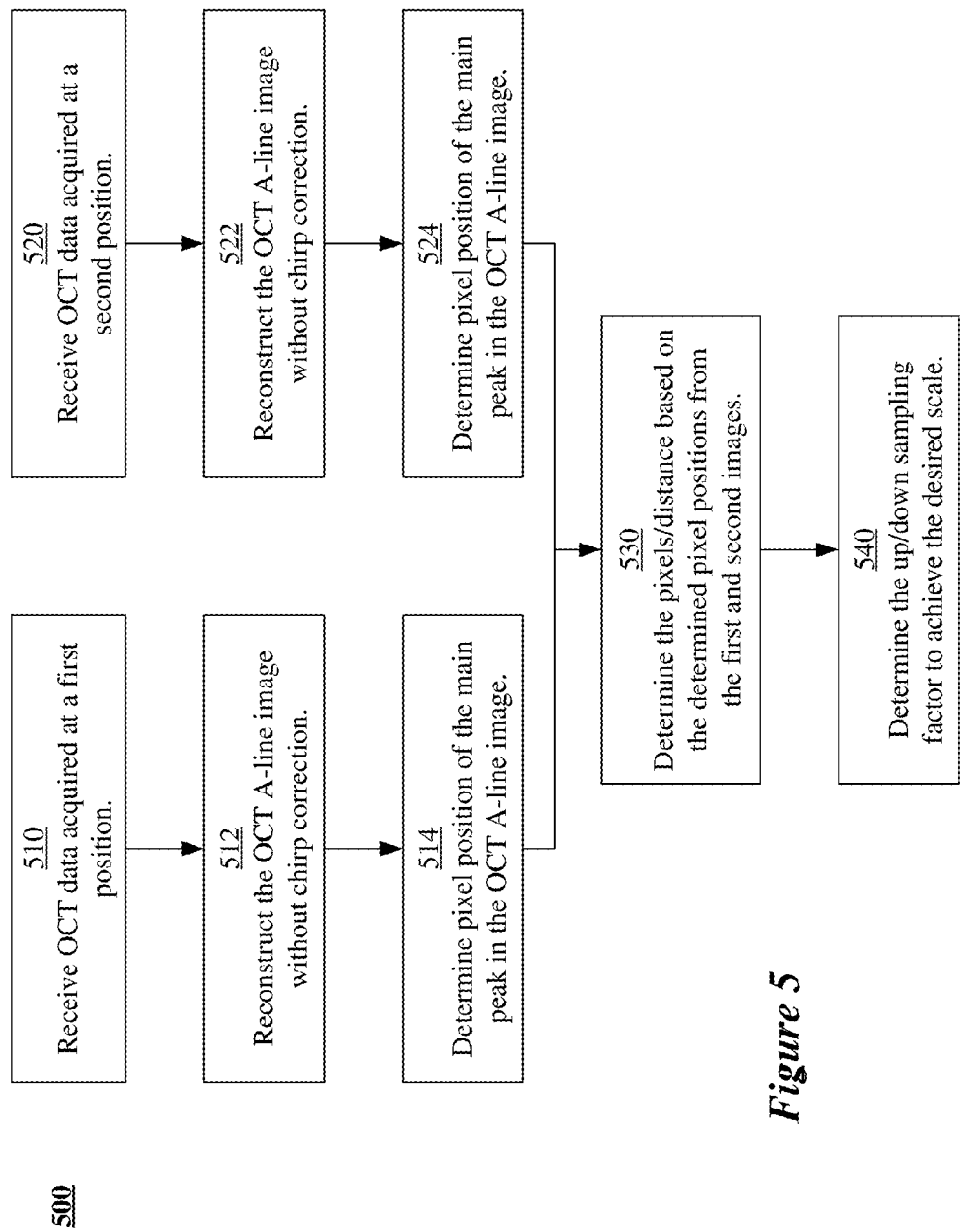
FIG. 5 illustrates a logic flow for a method of determining a sampling factor according to examples of the present disclosure.

FIG. 5 is a logic flow illustrating a method 500 for determining the up or down sampling factor utilized to achieve a specified digital range. The method 500 may begin at blocks 510 and 520. At blocks 510 and 520, OCT image data is received. In particular, at block 510, OCT image data acquired at a first location is received while at block 520, OCT image data acquired at a second location, a known distance from the first location, is acquired.

At blocks 512 and 522, the OCT A-line images corresponding to the received OCT image data at the first and second positions are reconstructed.

Figure 6:
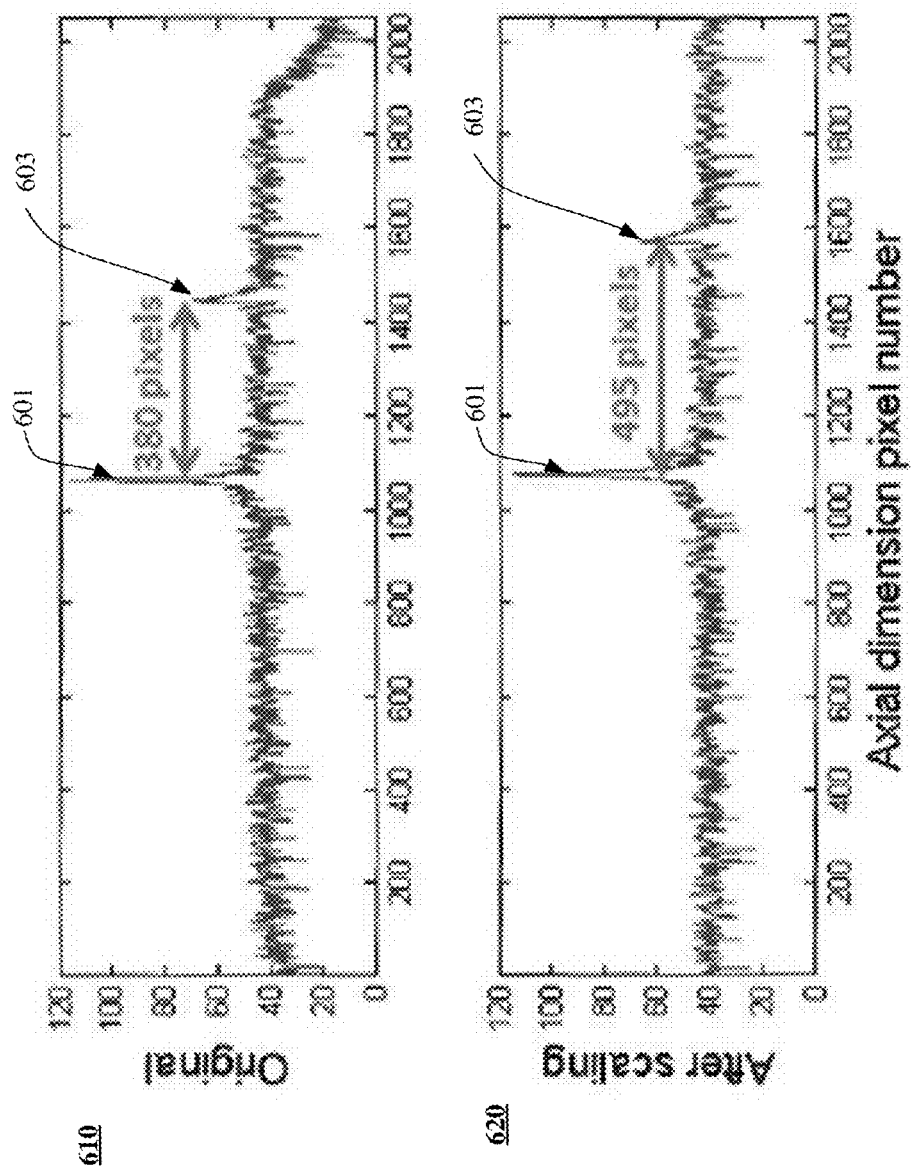
FIG. 6 illustrates an OCT image scaled according to examples of the present disclosure.

At blocks 514 and 524, a position (e.g., in pixels) of the main peak in the OCT A-line image is determined. At block 530, the scale (e.g., pixels/mm, pixels/inch, or the like) is determined. At block 540, an up or down sampling factor is determined. The up or down sampling factor can be used to transform the scale of the OCT image to a desired scale. For example, FIG. 6 illustrates an original OCT image 610 that has been scaled (e.g., using the method 500) to form a second image 620. As evidenced of this adjustment to the scale, the distance (e.g. in pixels, or the like) between features 601 and 603 in the images has been adjusted. More specifically, the distance has been increased. However, as will be appreciated, in some examples, the distance can be shortened. In some examples, the signal processor 210 may be configured to adjust the digital range (e.g., the scale) each time the OCT system is operated (e.g., at start-up). In this manner, drift in the optical properties of components of the OCT system 200 (e.g., through out the life of the system) can be compensated for. Thereby improving reliability and repeatability of OCT measurements and data over the operational life of the system. Furthermore, embodiments of the present disclosure allow significantly higher precision control over the axial image dimension in OCT systems.

C. Improved Image-Quality Stability

OCT systems can include a variety of features. Some features are required to maintain the imaging quality of the imaged medium, like Polarization-Diversity (PD) or Polarization Sensitive (PS) systems. Some features improve sensitivity by increasing the laser power at the medium. Other features are utilized to accommodate the design (e.g., an internal calibration arm for laser recalibration in more advanced swept-source lasers) or phase measurements. As will be appreciated, these features add to the complexity of the system and may require readjustment to compensate for environmental effects.

For example, higher laser powers at the sample often requires the use of optical circulators within the interferometer. The high polarization-mode dispersion (PMD) in typical circulators requires precise adjustment of the polarization state in the reference arm of PD-OCT and PS-OCT systems. In catheter-based systems, PD detection is primarily useful to eliminate the sensitivity to the dynamic polarization alterations in the constantly rotating catheter. This adjustment, however, is sensitive to the temperature of the system and stresses on the fiber optics, often causing system calibration to become invalid and axial resolution to be significantly compromised.

Embodiments of the present disclosure can be implemented to eliminate PMD in the reference and calibration arms, reduce the thermal variability of the OCT system, and reduce the sensitivity to changes on the stresses on the optical fibers in the system. In particular, an OCT system can be implemented to utilize 45° faraday rotators (FRs) in the reference and calibration arms. As will be appreciated, a 45° FR results in 90° rotation of the polarization state in delay lines with common-path configuration. As such, polarization alterations experienced by the light in one pass (e.g., due to PMD and/or thermal variation) are cancelled out in the second pass.

Figure 7:
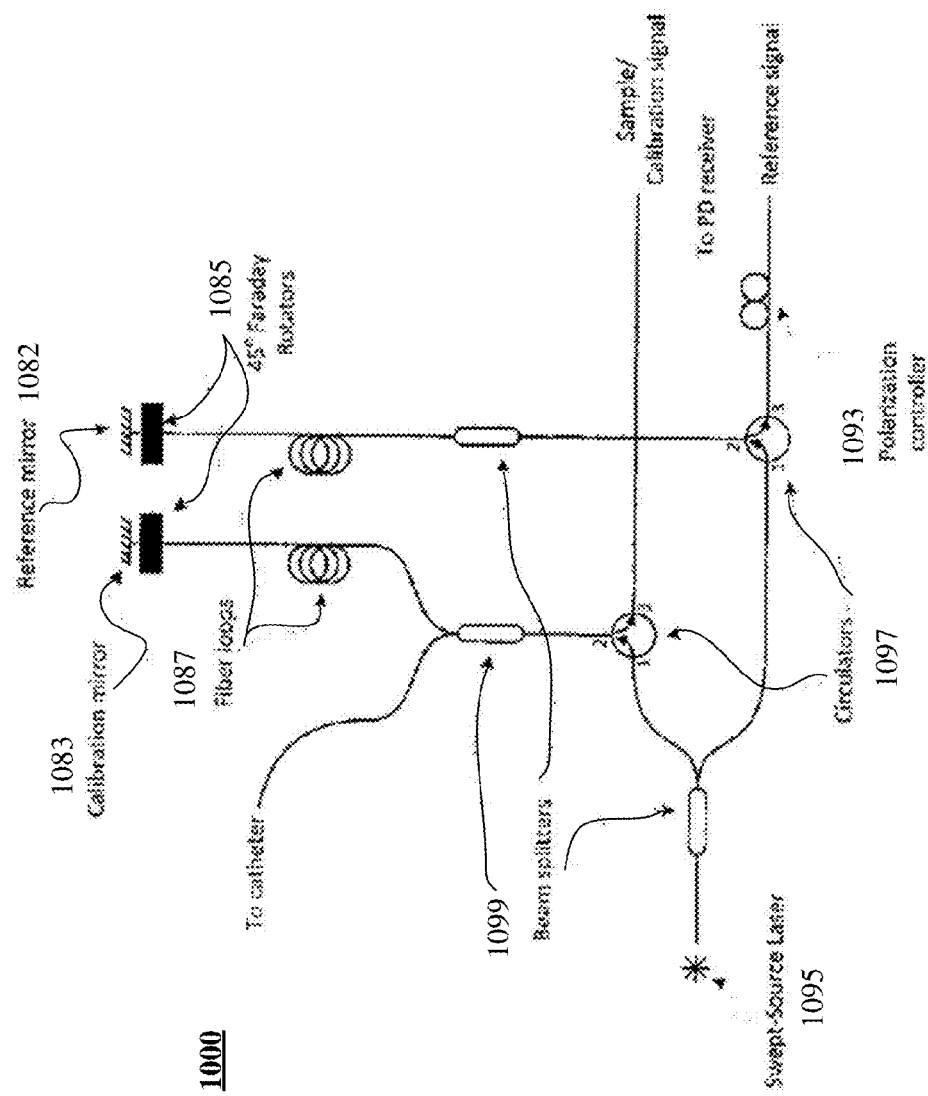
FIG. 7 illustrates an SS-Oct system arranged according to examples of the present disclosure.

FIG. 7 illustrates a SS-OCT system 1000 in accordance with various embodiments of the present disclosure. The system 1000 includes FRs 1085 and fiber loops 1087 incorporated within a reference arm (e.g., the reference arm 80 of FIG. 2) and a calibration arm (e.g., the calibration arm 84 of FIG. 2). As depicted, the FRs 1085 are disposed between the mirrors (e.g., the reference mirror 1082 and the calibration mirror 1083) and the fiber loops 1087 within each respective arm. FIG. 7 further depicts the source 1095, optical circulators 1097, optical beam splitters 1099 and a polarization controller 1093.

Figure 8B:
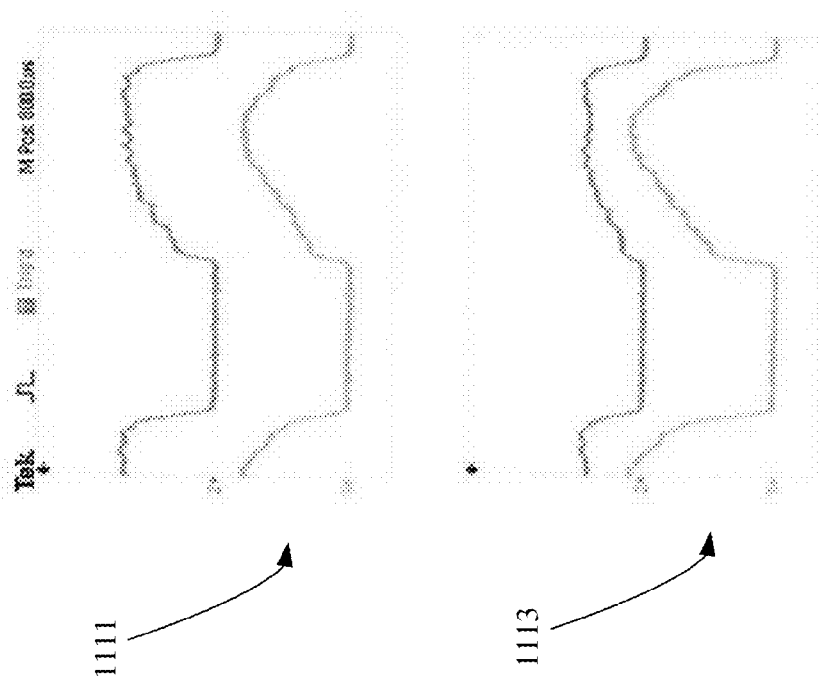
FIGS. 8A-8B illustrate traces of a reference arm signal.
Figure 8A:
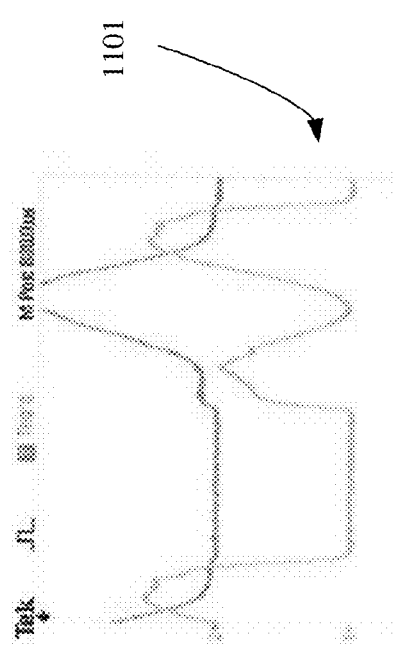

FIGS. 8A-8B show traces of the reference arm signals in PD-SS-OCT systems. In particular, FIG. 8A shows the signals from a conventional system while FIG. 8B shows the signals from a system arranged according to embodiments of the present disclosure (e.g., the system 1000). The signals correspond to signal taken at two different temperature readings. In particular, 20 degrees C. for the top signals and 35 degrees C. for the bottom signals. Specifically, the signals 1101 and 1103 are shown in FIG. 8A and the signals 1111 and 1113 are shown in FIG. 8B.

As is evident from signals 1101 and 1103, fluctuations (e.g., variance in the magnitude of the signals) within a single sweep may manifest in conventional systems. Such fluctuations generally lead to poor calibration due to low signal intensities at some parts of the sweep, as well as reduced axial resolution. Furthermore, as depicted in this figure, the PMD effect is temperature dependent; resulting in different scan fluctuations during scans taken at different temperatures.

FIG. 8B depicts signals 1111 and 1113 from a system with 45° FRs (e.g., the FRs 1085) added to the reference arm. As depicted, PMD is substantially eliminated in signals 1111 and 1113. Furthermore, the impact of thermal variability is significantly reduced. Eliminating the PMD effect in the reference arm improves the quality of system calibration and the axial resolution of the image. The absence of PMD in the calibration arm improves the calibration quality while eliminating the need to utilize another polarization-controller in the calibration arm. When a system with FRs is designed with the bulk of its fibers is in the common-path to and from the FRs, thermal stability is significantly improved, resulting in reliable recalibration and image quality.

D. Optical Shutter in the Fiber-Optic Rotary Junction

As will be appreciated, an option to block the sample (e.g., the sample 86) in catheter-based OCT systems is preferred for patient and operator safety, recording background data, and providing feedback on the optical transmission quality of the front-end of the OCT system. More specifically, an option to block light from being incident on the sample is desired.

Embodiments of the present disclosure may accomplish sample blocking by implementing an optical shutter in the sample path. As will be appreciated, OCT systems are typically implemented using fiber optics. Fiber optic shutters can include mechanical, electo-optical, or acousto-optical shutters, which may be added to the free-space of the light path. However, such techniques generally introduce optical losses to the sample path, resulting in degradation of the image quality. Typical shutter loss varies between 1-3 dB, yielding 2-6 dB of degradation on the image quality (e.g., due to the signal propagation from the source 95 to the sample 86 and back to signal processor 210).

Figure 9:
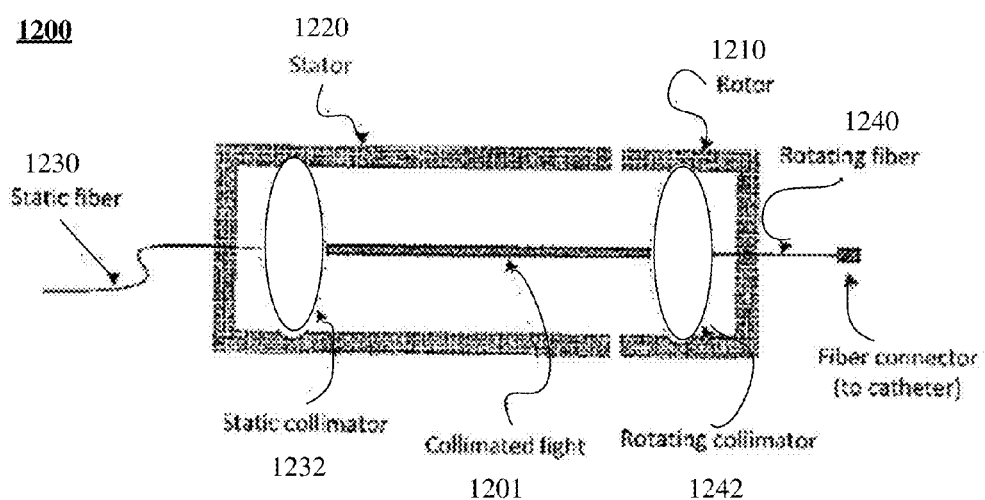
FIG. 9 illustrates a conventional fiber optic rotary joint.

In catheter-based OCT systems, the FORJ is a natural place where the fiber optic path is altered to allow coupling the light between the system and the rotating catheter. For example, a static collimator lens mounted to the stator can collimate light entering a FORJ through a fiber optic cable. The rotating collimator on the rotor couples the collimated beam into a fiber that connects to the catheter. For example, FIG. 9 illustrates a conventional FORJ 1200. As depicted, the FORJ 1200 includes a rotor 1210, which is typically attached to a stator 1220 by means of a bearing (not shown). Accordingly, light (e.g., collimated light 1201) may be communicated from the static fiber 1230 to the rotating fiber, and the fiber connected catheter 1240 via the static collimator 1232 and the rotating collimator 1242.

Figure 10A:
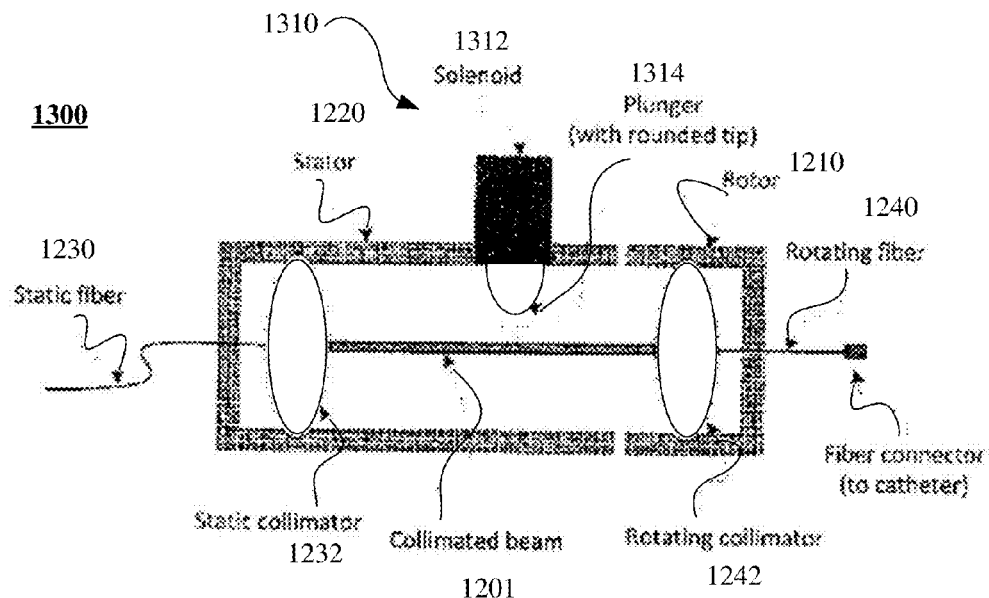
FIGS. 10A-10B illustrate fiber optic rotary joints arranged according to examples of the present disclosure.
Figure 10B:
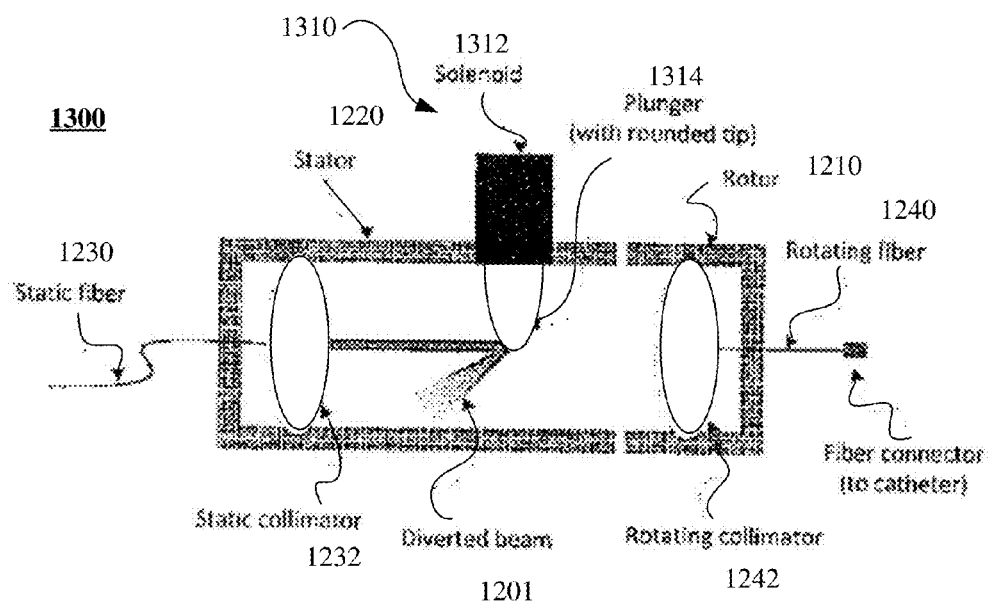

FIGS. 10A-10B illustrates a FORJ 1300, including a mechanical shutter 1310, arranged according to some embodiments of the present disclosure. It is noted, that the FORT 1300 may be provided without introducing additional optical loss into the OCT system (e.g., the system 200). In some examples, the mechanical shutter 1310 may be implemented with a pull-type electromechanical solenoid 1312. The solenoid 1312 may be configured to introduce and clear a plunger 1314 to/from the path of the collimated light 1201; thereby allowing bidirectional coupling of the light to and from the catheter.

In some examples, the plunger 1314 of the solenoid 1312 blocks the optical beam travelling from the stator 1220 to the rotor 1210 of the FORJ 1300 (e.g., refer to FIG. 10B) when the solenoid is "unpowered". In particular, the plunger 1314 is placed to fully block the light beam 1201. In some examples, the stroke length of the solenoid 1312 is chosen to completely clear the optical path when powered. With some examples, the stroke is length is equal to or slightly larger than the diameter of the beam 1201.

It is noted, that the FORJ 1300 may be implemented in a "normally-closed" or a "normally-open" configuration. However, in some example, the FORJ 1300 may be implemented normally-closed to enhance patient and operator safety.

Electromechanical solenoid valves may lose pull force at higher temperatures and may generate heat when actuated for extended times. To reliably open the shutter, the solenoid is preferably actuated with a high drive voltage (e.g., twice the full-duty-cycle voltage) for 1-2 seconds. To minimize the heat generation in the solenoid, the drive voltage is preferably dropped to a low level (e.g., one-half of the full-duty-cycle voltage).

In order to utilize the FORT shutter for OCT background data collection, low levels of back reflection are preferably maintained when the shutter is closed. Low back reflection is accomplished in embodiments of the disclosure by tapering or rounding the tip of the plunger and blocking the light with the tip. As such, the reflected light is diverted away from the incident beam (e.g., as shown in FIG. 10B). To reduce or eliminate back-reflection of light back out of the stator, the radius of the sphere, in the rounded-tip configuration, is preferably larger than the beam diameter. Thus, embodiments of the disclosure allow the shutter to block an optical beam with high laser power without special surface treatment, making it suitable even for laser-marking applications.

The placement of the shutter before the rotating collimator 1242 of the FORT 1300 may be done to allow collection of appropriate background data. Furthermore, it may allow the system to self-test for the cleanliness of the front-end of the system (i.e., the fiber connector where catheters connect to the system), which may experience more contamination.

Figure 11A:
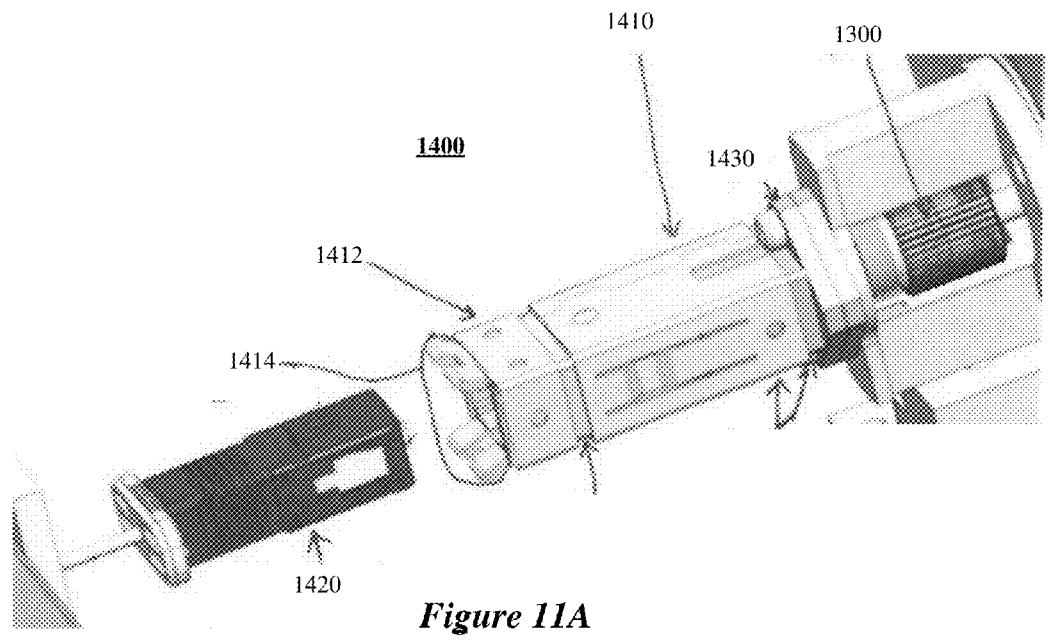
FIGS. 11A-11B illustrate perspective views of an intermediate optical connection assembly arranged according to examples of the present disclosure.
Figure 11B:
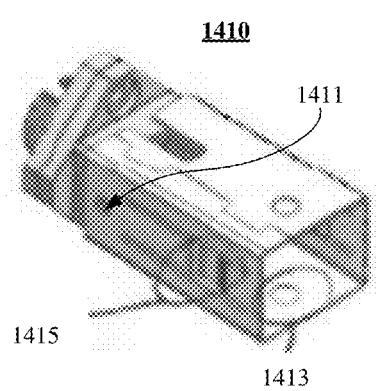

E. Optical Interconnect Stabilizer Alignment Adapter for Repetitive Optical Connections FIGS. 11A-11B illustrate perspective views of an intermediate optical connection assembly 1400. The intermediate optical connection assembly 1400 can be used to connect the FORJ 1300 to a catheter 1420 (or more specifically to an internal optical connector 1420 of a catheter). In general, the intermediate optical connector 1400 can be, for example, include a O-dB optical connector, an optical and electrical connector, or the like. In conventional OCT systems, the FORJ is connected to a catheter with an assembly having an outer and inner housing, which float and are aligned internally only when a connection is made to both sides of the connector. As such, the connection may be in a different position for every load and unload. More specifically, the internal optical connector may be in a different position every time a catheter is connected.

Various embodiments of the present disclosure provide the intermediate optical connection assembly 1400 having an intermediate optical connector 1410 and alignment adapter 1412. The assembly 1400 can be repeatedly connected without changes to the alignment of the connector. In general, the connector 1410 is mounted (e.g., via glue, weld, or built into the piece) on a bulkhead 1430. The bulkhead 1430 corresponds to the junction mating the FORJ 1300 to the intermediate optical connector 1410. With some examples, the intermediate optical connector 1410 is made to be a serviceable item; since damage or debris may contaminate the connection made with a catheter. Accordingly, the intermediate optical connector 1410 of the present disclosure may be taken out and a clean and damage-free connector put in.

Furthermore, the intermediate optical connector 1410 can be constrained mechanically to reduce motion of the outer housing while the inner housing still floats so a precision alignment will happen with the optical interfaces. Since the outer housing is constrained, it will be in the same location during load and unload (e.g., connection and un-connection of the catheter 1420, or the like) making for a more well aligned connection with less wear on the components.

Embodiments of the present disclosure also address the alignment of the catheter 1420. As will be appreciated, the catheter handle has an optical connector that floats within the handle. These tolerances (e.g., in X, Y, and rotation, or the like) may be too large for a consistent connection to be made using conventional techniques. Accordingly, the present disclosure may provide the alignment adapter 1412 attached to the front of the intermediate optical connector 1410. The alignment adapter 1412 is configured to funnel the male part of the catheter 1420 into the female receptacle of the intermediate connection 1410. The alignment adapter 1412 aligns the X, Y, and rotation of the optical connection of the catheter 1420 (e.g., via alignment tabs 1414, or the like) for a consistent and reliable connection to the FORJ 1300.

Overall, the intermediate optical connector 1410 and the alignment adapter 1412, in combination, provide an intermediate connection between the FORJ 1300 and the catheter 1430.

Turning more specifically to FIG. 11B, an example of the intermediate connector 1410 is shown. The connector 1410 may include a number of bonding holes 1411. The bonding holes 1411 can be used to secure (e.g., via glue, epoxy, welding, mechanical attachment, or the like) the connector 1410 to the bulkhead 1430. Additionally, the connector 1410 may include an indentation 1413 and/or spring 1415 configured to stabilize the front of the catheter 1420 when it is connected to the connector 1410.

F. Linear Interpolation of Complex Numbers for Non-Linear SS-OCT Imaging Systems As will be appreciated, frequency-domain OCT encodes the depth of scattering features in the frequency of the recorded signal. Accordingly, to obtain a spatial image, OCT techniques rely heavily on a digital implementation of the Fourier transform. As swept sources and acquisition systems become increasingly fast, it is increasingly necessary for the Fourier transform to be implemented efficiently.

Embodiments of the present disclosure utilize the digital Fast Fourier transform (DFFT). The DFFT typically requires samples to be equally spaced in frequency space for optimal performance. In software-based correction of the swept source non-linearity, once the non-linearity of the swept source is characterized, resampling of the digitally acquired data is performed using interpolation.

Linear interpolation is the most straightforward and commonly used method, but it may suffer from severe artifacts and side lobes when signal depth is far removed from the O-delay position. More elaborate interpolation schemes are possible, but their implementation is more complex.

Linear interpolation is a well-defined mathematical process for a one-dimensional real function. Linear interpolation of continuous functions on an n-dimensional space, with n greater than 1, is generally not well defined. Effectively, a complex function is defined in a two-dimensional space (the real and the imaginary axis) for purposes of interpolation. Traditionally, linear interpolation of complex signals, as used in frequency-domain OCT, assumes that one may perform linear interpolation independently on the x-axis (the real part of the complex number) and the y-axis (the imaginary part of the complex number).

Because the non-linearity of the swept-source is characterized by looking at the phase of complex numbers, embodiments of the invention implement linear interpolation of complex numbers by considering the magnitude and phase as the two independent functions. That is, the radius r and angle <p in the complex plane, rather than x and y.

Figure 12:
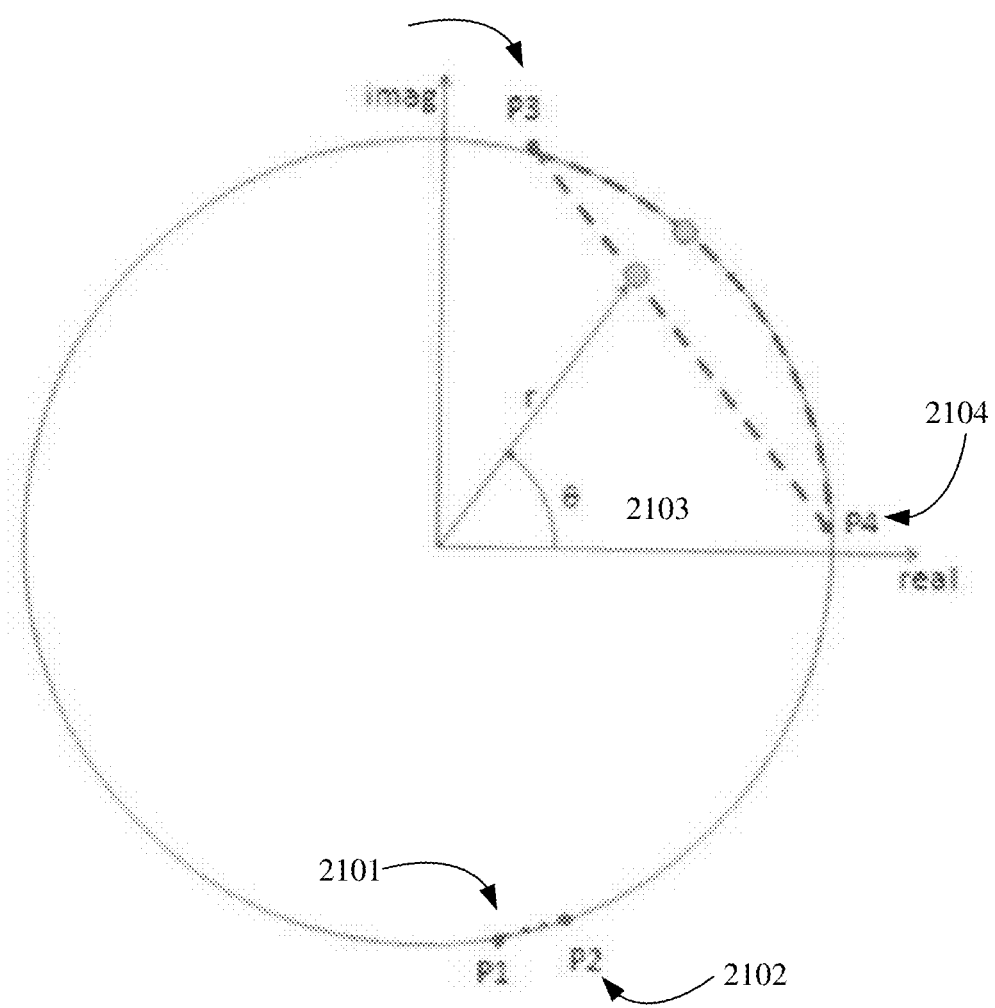
FIG. 12 illustrates an example of linear interpolation of a signal arranged according to examples of the present disclosure.

For a typical signal, where the amplitude of the signal is expected to vary slower than the phase, as shown in FIG. 12, linear interpolation of a signal is more accurate when utilizing polar coordinates, as compared to rectangular coordinates. As depicted, two close points 2101 and 2102 (P1, P2) will yield substantially similar results using both techniques, while two distant points on the circle 2103 and 2104 (P3, P4) will yield more accurate results when the linear interpolation is performed utilizing polar coordinates.

G. Control and Manipulation of Image Data

Medical systems that acquire and produce image data have rapidly improved through increased signal-to-noise, contrast and spatial resolution. Improvements in resolution alone have resulted in cross-sectional modalities such as Ultrasound, MRI and CT, producing hundreds of images per procedure that need to be reviewed in an easy and efficient manner. OCT is a recent optical imaging modality that provides high-resolution cross-sectional images of tissue microstructure. A typical "scan" of an esophagus using a catheter based OCT system can produce more than 1000 images. Without appropriate functionality to control and manipulate the images, review of such a volumetric dataset can be tedious.

Figure 13:
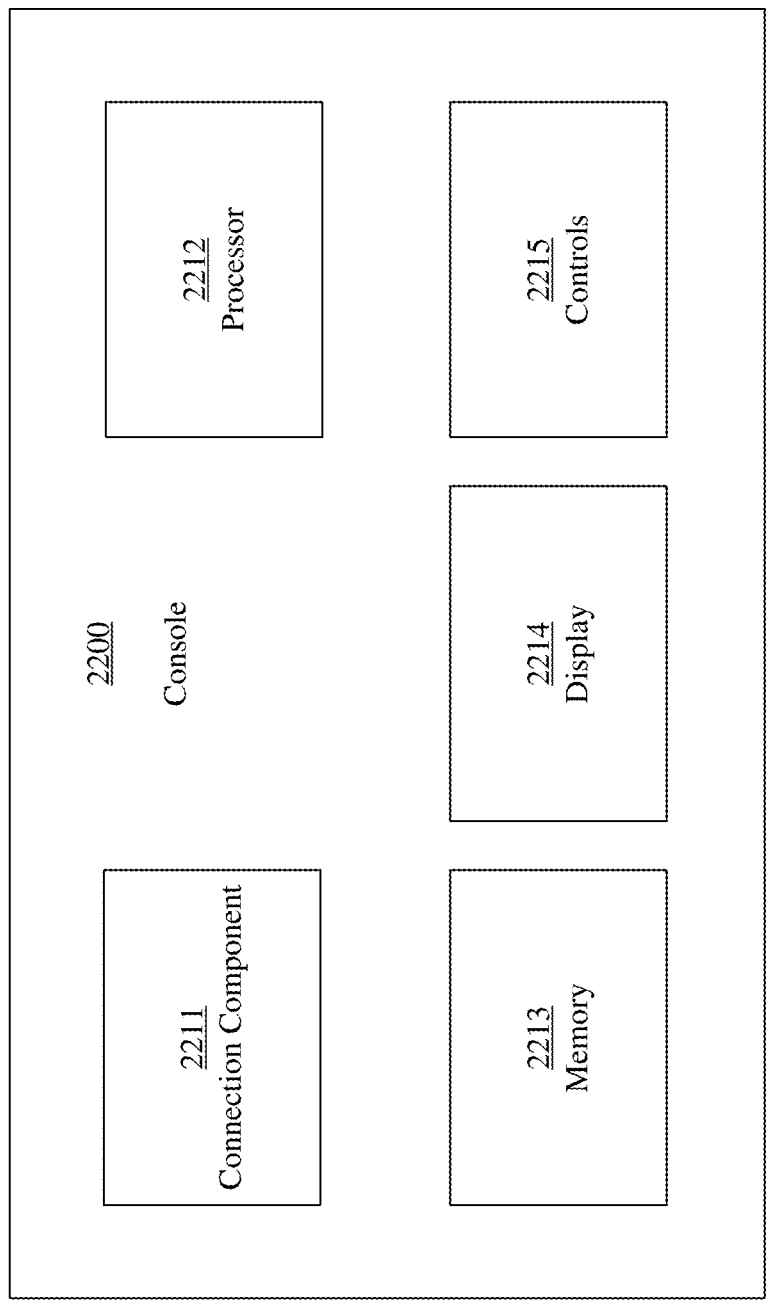
FIG. 13 illustrates a console for an imaging system arranged according to examples of the present disclosure.

Embodiments of the present disclosure enable fast and discrete review of image data utilizing one or more of the following techniques. In particular, the present disclosure may provide a graphical user interface, controls, and associated functionality to enable a user to efficiently review such datasets. FIG. 13 illustrates a block diagram of a portion of an OCT system that may be implemented according to various examples of the present disclosure. In particular, FIG. 13 depicts a console 2200 having a connection component 2211, a processor 2212, a memory 2213, a display 2214, and controls 2215.

The connection component 2211 may be configured to receive optical and/or electronic data corresponding to OCT image data. The processor 2212 may be a general purpose processor and/or a special purpose processor configured to implement the logic and functionality detailed herein. The memory 2213 may be a variety of types of memory, including non transient memory configured to store data (e.g., OCT image data) and instructions for processing and execution by the processor 2212. The display 2214 may be configured to display OCT image data and the controls 2215 may be configured to receive input from a user. In some examples, the display and the controls may be implemented as a single device (e.g., a touch screen, or the like).

FIGS. 14A-14D illustrate example displays of OCT image data, arranged according to various embodiments of the present disclosure. It is noted that the displays may be generated and/or manipulated using the console 2200.

Figure 14A:
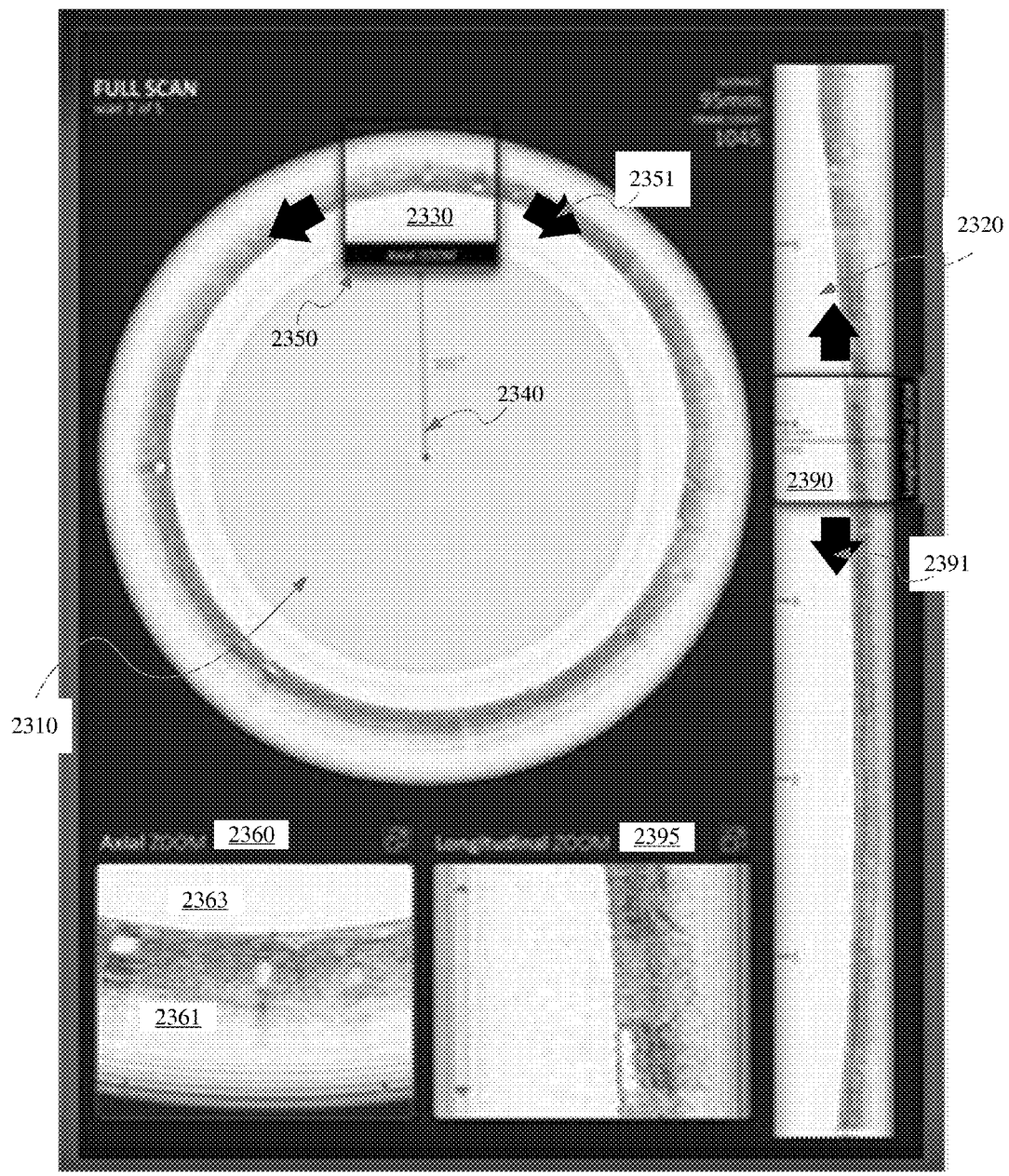
FIGS. 14A-14D illustrate interactive displays arranged according to examples of the present disclosure.

Turning more specifically to FIG. 14A, a display 2301 may be organized to display of various portions of imaging data taken from within a bodily lumen (e.g., an esophagus). In various embodiments, such data may be considered to substantially correspond to a cylinder having a length corresponding to the length along which measurements were taken and a thickness corresponding to the imaging depth (i.e., the depth of the lumen from which images are acquired). The display 2301 may include an axial scan region 2310 for displaying a single axial slice of the data and a longitudinal scan region 2320 for displaying all or a portion of a longitudinal slice of the data. Since a longitudinal slice of cylindrical data typically corresponds to two roughly linear and/or rectangular portions (i.e., one on either side of the central axis of the cylinder), the longitudinal scan region 2320 may display only one of these portions of the data, as shown in FIG. 14A.

The display 2301 may also incorporate a rotating handle 2330 composed of a tether 2340 connected to a window 2350. As indicated by the arrows 2351 in FIG. 14A, the handle 2330 may rotate about the center the axial scan region 2310. In particular, as one end of the tether 2340 is fixed to the center of the circular axial scan region 2310, the windows 2350 will rotate about the edge of the axial scan region 2310 to a desired portion of the axial scan data (which, as shown, is typically located on the outer edge of the circular scan area). The portion of the axial scan data within the window 2350 may be enlarged and displayed in an axial zoom region 2360.

In some embodiments, the axial zoom region 2360 displays the portion of the axial scan data in a fixed orientation (e.g., a tissue region 2361 below an air region 2363) regardless of the position of the window 2350. As is clear from FIG. 14A, the portion of the image within the window 2350 will typically have a different orientation than the version displayed within axial zoom region 2360 (except for, e.g., when the window 2350 is located at the "bottom" of the cylindrical data displayed in the axial scan region 2310).

In some examples, the processor 2212 may determine the angle to rotate the image in the axial zoom region 2360 based on the angle of the tether 2340.

Furthermore, the display 2301 may incorporate a sliding window 2390 within the longitudinal scan region 2320. As indicated by the arrows 2391, the sliding window 2390 may be translated along the image displayed in the longitudinal scan region 2320, and an enlarged version of the image portion bounded by the sliding window 2390 may be displayed in a longitudinal zoom region 2395.

In some examples, a region of interest (ROI) within either the region 2310, 2320, 2360, and/or 2395 may be linked. More specifically, adjustment of the ROI in one region (e.g., the region 2360) may correspondingly adjust the ROI in another region. For example, movement of the window 2350 may correspondingly cause window 2320 to update to a new longitudinal image corresponding to window 2350's orientation. Likewise movement of the window 2390 may correspondingly cause the axial slice 2310 to update based on the position of 2390.

Figure 14B:
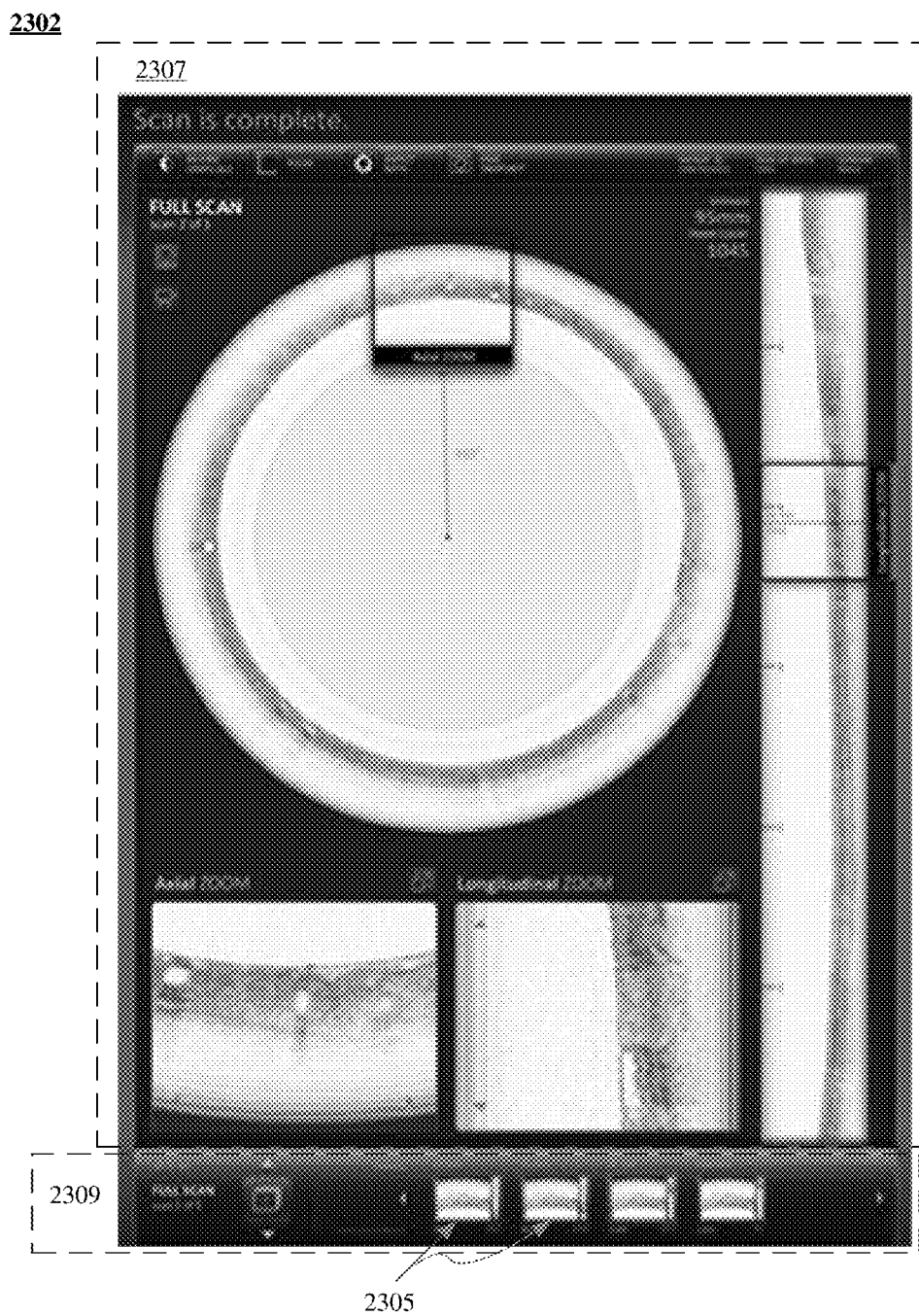

Turning more specifically to FIG. 14B, another example of a display 2302, also referred to as a snapshot panel, is depicted. As depicted, the display 2302 includes a main display portion 2307 and a snapshot panel 2309. The snapshot panel 2309 may include a series of snapshots or thumbnails 2305 corresponding to selected portions of the data displayable within the main display portion 2307.

For example, each thumbnail 2305 may display a small version of the image shown in the axial zoom region 2360 at a point selected by the user (e.g., corresponding to a feature of interest). Numerical indications of the rotation angle of the tether 2340 or approximate clock face time where 12 o'clock corresponds to 0°, the distance along the longitudinal view of the data, and/or the "frame count" (i.e., the one of the series of individual frames of data utilized to display the various views on display 2301) may be displayed for each thumbnail 2305. The thumbnail 2305 may also incorporate an icon indicating the relative position of the sliding window 2390 within the longitudinal scan region 2320 when the thumbnail 2905 was taken. Each thumbnail 2305 can also act as a bookmark, where clicking on the thumbnail will reposition each of the views to their respective position.

Figure 14C:
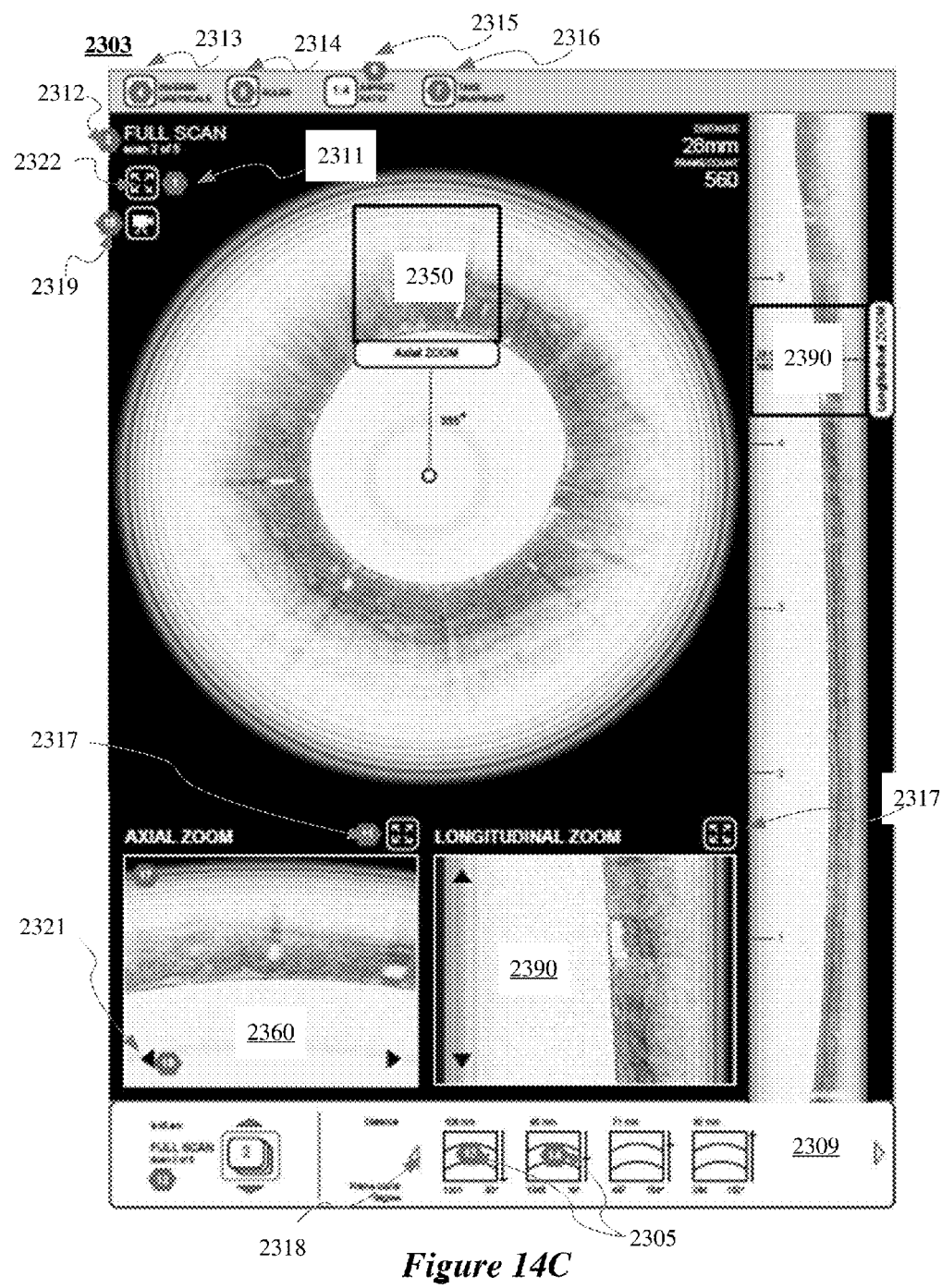

Turning more specifically to FIG. 14C, an example display 2303 is shown. The example display 2303 illustrates various features that may be incorporated into displays according to the present disclosure. For example, the display 2303 may include information related to the patient from whom the imaging data is received, such as, e.g., a patient name or identification number, year of birth, gender, or the like.

The display 2303 may also include a window 2312 configured to display the number of the displayed scan (of a number of different scans from the same patient, for example). The display may also include a button 2313 (e.g., toggle button, or the like) configured to change the colors (e.g., including gray scale, inverse gray scale, or the like). The display may also include an additional button to switch between the full A-line display (expanded field of view) or just the central section of the A-line (magnified field of view). Furthermore, the display 2303 may include a button 2314 (e.g., toggle button, or the like) configured to enable or disable the view of rulers (e.g., refer to FIG. 14D) indicating the scale of the various views. In addition, an angular Registration button can be available which allows the user to rotate the current OCT image about its central cylindrical axis to visually align it with the optical probe's current orientation within the patient. If in acquisition mode, the last angular registration will be inherited by further scans of the same optical probe.

Additionally, the display 2303 may include a feature to change or modify the aspect ration of the displayed images, such as, for example, with button 2315. Furthermore, the display 2303 may include a button 2316 configure to take a thumbnail when the window 2350 and window 2390 are positioned over an area of interest.

The sliding window 2390 may be moved (e.g., via user interaction with a touch screen or a cursor, or the like). The images shown in the axial zoom region 2360 or the longitudinal zoom region 2395 may be enlarged to occupy a larger portion (or even substantially all) of the display 2303 via operation of a one of the zoom buttons 2317.

Previous scans of the same optical probe (and optionally the time at which they were taken) may be displayed in the left snapshot portion of the display 2303 by selecting the up and down arrows. The current scan number is displayed in between the arrows. If the number of snapshots overflow the right portion then the user can scroll through the list with arrows 2318.

A video sequence of a section or all of the axial images through the data set may be recorded with button 2319. Furthermore, the axial zoom region 2360 and/or the longitudinal zoom region 2390 may include arrows 2321 to move the corresponding windows (e.g., 2350, 2360, or the like) and thus alter the scene displayed in region 2360 and/or 2390.

Figure 14D:
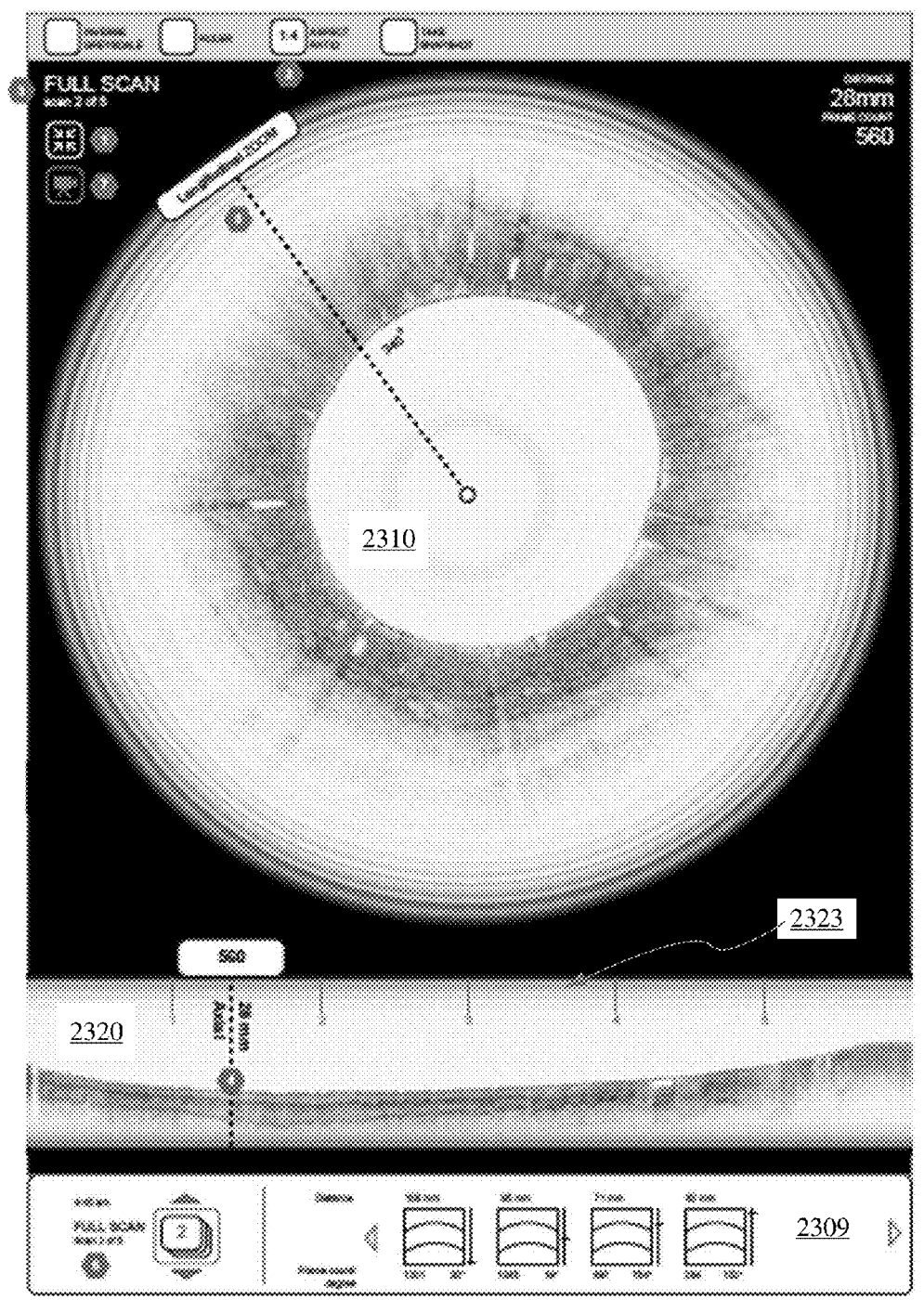

Furthermore, a zoom button 2322 may be utilized to change the display 2303 to an expanded axial display. For example, FIG. 14D illustrates a display 2304, which may correspond to an expanded axial display. As depicted, in the display 2304, enlarged versions of the axial scan region 2310, a horizontal longitudinal scan region 2320, and the snapshot panel 2309 may be displayed. Furthermore, FIG. 14D depicts sliding or rotating rulers 2323, which may indicate the scale of the displayed images. In some examples, the rulers 2323 may be calibrated based on intraoperative information such as distance of imaging device from an anatomical site of interest.

H. Monitoring the Balance of the Polarization Channels in the Reference Arm of Polarization-Diversity OCT In various embodiments, the quality of OCT images is optimized when the polarization states of the sample and reference light are matched. Maintaining the polarization state in the light collected from the sample is typically difficult or impossible when the sample is birefringent or polarization scrambling. Additionally, maintaining the polarization state in the light collected from the sample can be difficult when the sample fiber is constantly moving, such as, in catheter-based systems.

In these cases, Polarization-Diversity (PO) may be utilized to maintain the reflectivity image quality regardless of the polarization state of the sample light. PO maintains equal components of two orthogonal polarization states (e.g., P and S) in the reference light, which is accomplished by means of a polarization controller in the reference path.

However, environmental changes, like stress and temperature on the fibers of the reference path, may alter the set polarization state. This may significantly impact the image quality by lowering the signal-to-noise ratio (SNR), even reducing it substantially to zero in some instances. Thus, there is a need for the ability to monitor the P-S balancing (i.e., the balancing of the two orthogonal polarization states) in PO-OCT.

Balance-Detection is widely utilized in SSOCT to improve system sensitivity. However, BD rejects the signal carrying the laser sweep profile, eliminating the information required for PS balancing monitoring.

Figure 15:
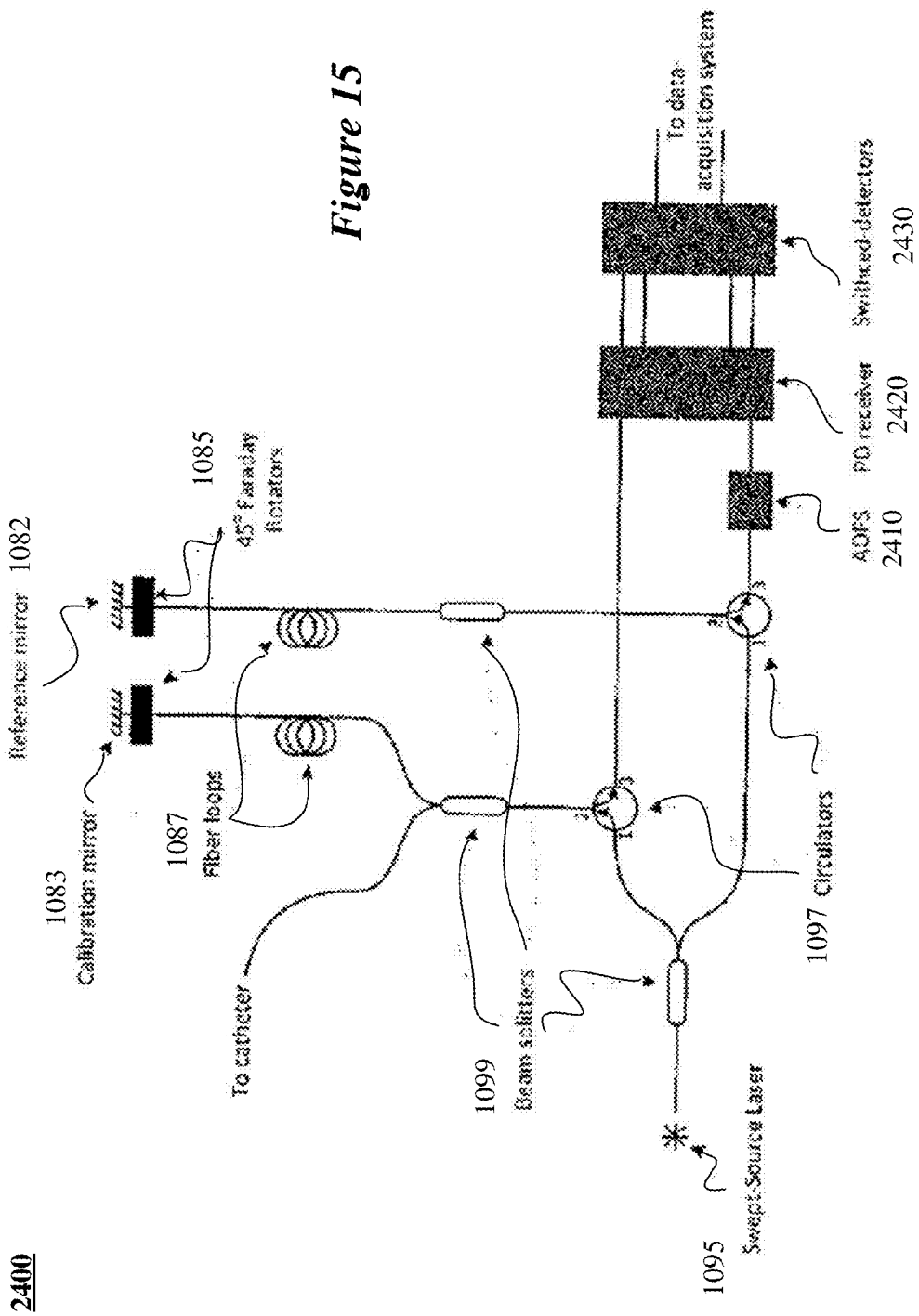
FIG. 15 illustrates an OCT system implementing P-S balance monitoring arranged according to examples of the present disclosure.
Figure 16:
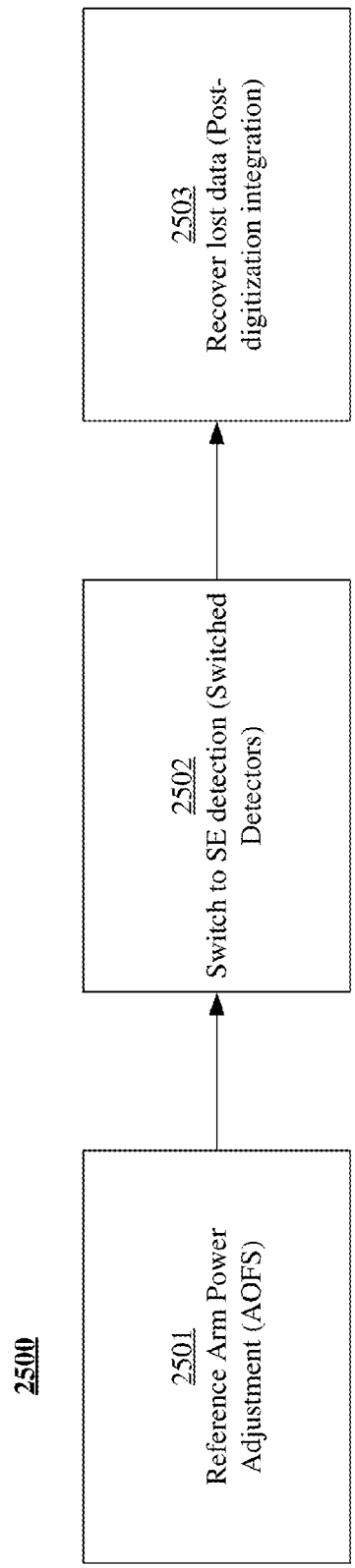
FIG. 16 illustrates a logic flow of a method for implementing P-S balance monitoring of an OCT system arranged according to examples of the present disclosure.

Embodiments of the present disclosure monitor the P-S balance in a swept-source (SS) PO-OCT system and/or Single-Mode Fiber-Based Polarization-Sensitive SSOCT systems. In some examples, as shown in FIGS. 15-16, the P-S balance monitoring is implemented in three stages: switch for single-ended detection, dynamic reference arm attenuation, and data recovery. In general, FIG. 15 depicts a system 2400 for implementing P-S balance monitoring while FIG. 16 illustrates a method 2500 of P-S balance monitoring, which may be implemented by the system 2400.

Turning more specifically to FIG. 15, the system 2400 includes components of the system 1000 described above in conjunction with FIG. 7. In particular, the system 2400 includes a source 1095, circulators 1097, beam splitters 1099, fiber loops 1087, FRs 1085, and reference and calibration mirrors 1082 and 1083.

Furthermore, the system 2400 includes an Acousto-Optic Frequency Shifter (AOFS) 2410, a PD receiver 2420, and switched detectors 2430. In general, single-ended (SE) detection is utilized in various embodiments of the disclosure to monitor the laser sweep profiles on the two channels (e.g., the reference and calibration channel). SE is accomplished by adding Radio-Frequency (RF) switches (e.g., switched detectors 2430) to the output of the OCT detectors. The switched detectors 2430 toggle between the imaging mode (e.g., using BD), and monitoring mode (e.g., using SE). In some examples, the switched detectors 2430 may be implemented with the normally-closed position connecting the BD to the output, thus allowing the system to image in the case of switch failure.

Balanced-detection may be also implemented by inserting a switch (not shown) to the frontend of the detectors, before the signal is amplified, or by inserting optical switches before the photodiodes. In contrast with the implementation described above, these implementations typically do not require separate circuitry for SE detection. However, the use of optical switches may result in some degradation of the OCT sensitivity.

Dynamic attenuation in the reference arm is utilized to adjust the power at levels observable by the detectors when switching between the BD and SE modes. The detectors may saturate or detect signals with low SNR if the power level is not adjusted. Optical power level adjustment may be accomplished by controlling the amplitude of the RF signal applied to the AOFS 2410. As depicted, the AOFS 2410 is disposed in the reference arm (e.g., the arm 80). The AOFS 2410 can also be used in embodiments of the disclosure to frequency-shift the OCT signal to remove depth ambiguity, as detailed herein.

Turning more specifically FIG. 16, the method 2500 includes block 2501-2503. At block 2501, the power of the signal in the reference arm may be amplified (e.g., by the AOFS 2410, or the like). At block 2502, SE detection may be turned on (e.g., by the switched detectors 2430, or the like). In some examples, the system 2400 may be implemented with high-pass filters to eliminate low frequency signals. As will be appreciated, the cut-off frequency of such filters may be sufficiently high to filter out the low-frequency laser sweep information. Thus, at block 2503, a data recovery scheme is implemented to restore any lost information due to the filter.

High-pass filtering is equivalent to applying a derivative to the signal. Therefore, in some embodiments, the signal is integrated post-digitization to recover any lost data. Simple integration yields sweep curves that may not be perfectly representative of the original laser seep shapes; however, the curves are generally sufficient to evaluate the balancing of the two channels.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of displaying images of a lumen acquired using an imaging modality, the method comprising the steps of:
   generating an axial scan region including an axial slice of an image of the lumen;
   generating an axial zoom region, the axial zoom region including an enlarged axial slice of a first portion of the image of the lumen;
   generating a longitudinal scan region including a longitudinal slice of the image, wherein the longitudinal slice corresponds to the axial slice;
   generating a longitudinal zoom region, the longitudinal zoom region including an enlarged longitudinal slice of the first portion of the image of the lumen;
   displaying the axial scan region, the longitudinal scan region, the axial zoom region, and the longitudinal zoom region on a display device;
   overlaying a first window on a portion of the axial scan region; and
   overlaying a second window on a portion of the longitudinal scan region;
   wherein the portion of the axial scan region and the portion of the longitudinal scan region correspond to the first portion of the image displayed in the axial zoom region and the longitudinal zoom region.

2. The method of claim 1, further comprising:
   receiving an input including an indication of a movement of the first window;
   adjusting the position of the second window based on the movement of the first window;
   updating the enlarged axial slice displayed in the axial zoom region based on the movement of the first window; and
   updating the enlarged longitudinal slice displayed in the longitudinal zoom region based on a movement of the second window.

3. The method of claim 1, further comprising:
   receiving an input including an indication of a movement of the second window;
   adjusting the position of the first window based on the movement of the second window;
   updating the enlarged axial slice displayed in the axial zoom region based on a movement of the first window; and
   updating the enlarged longitudinal slice displayed in the longitudinal zoom region based on the movement of the second window.

4. The method of claim 1, further comprising adjusting an orientation of the enlarged axial slice displayed in the axial zoom region to have a fixed orientation.

5. The method of claim 1, further comprising transmitting data including indications of the axial scan region, the longitudinal scan region, the axial zoom region, and the longitudinal zoom region to a display device.

6. A method of displaying images of a lumen acquired using an imaging modality, the method comprising the steps of:
   generating an axial scan region including a representation of an axial slice of an image of the lumen;
   generating an axial zoom region, the axial zoom region including a representation of an enlarged axial slice of a first portion of the image of the lumen; and
   scaling the representation of the axial slice of the image of the lumen, the scaling including:
      reconstructing a first image;
      reconstructing a second image;
      determining a first position of a main peak in the first image;
      determining a second position of the main peak in the second image;
      determining a scale corresponding to the first and the second image based at least in part on the determined first and second positions; and
      determining an up or down sampling factor to adjust the scale of the first and the second image to a desired scale.

7. The method of claim 6, further comprising:
   generating a longitudinal scan region including a representation of a longitudinal slice of the image, wherein the longitudinal slice corresponds to the axial slice; and
   generating a longitudinal zoom region, the longitudinal zoom region including a representation of an enlarged longitudinal slice of the first portion of the image of the lumen.

8. The method of claim 7, wherein the step of scaling the representation of the axial slice of the image of the lumen comprises compressing the image.

9. The method of claim 7, wherein the step of scaling the representation of the axial slice of the image of the lumen comprises expanding the image.

10. The method of claim 6, wherein the first image is an image of a calibration mirror captured at a first location and the second image is an image of the calibration mirror captured at a second location, the second location a known distance from the first location, and wherein the step of determining a scale corresponding to the first and the second image is based at least in part on the known distance.

11. The method of claim 6, wherein the first image and the second image are reconstructed without any processing steps that alter the image scale.

12. The method of claim 6, wherein the first image is an image of a lumen captured at a first location and the second image is an image of the lumen captured at a second location, the second location a known distance from the first locations, wherein the main peak corresponds to a phantom in the first and second images, and wherein the step of determining a scale corresponding to the first and the second image is based at least in part on the known distance.

13. At least one non-transitory machine-readable storage medium comprising instructions that when executed by a computing device, cause the computing device to:
   generate an axial scan region including an axial slice of an image of a lumen acquired from an imaging modality system;
   generate an axial zoom region, the axial zoom region including an enlarged axial slice of a first portion of the image of the lumen;
   generate a longitudinal scan region including a longitudinal slice of the image, wherein the longitudinal slice corresponds to the axial slice; and
   generate a longitudinal zoom region, the longitudinal zoom region including an enlarged longitudinal slice of the first portion of the image of the lumen,
   wherein the first portion of the image of the lumen corresponds to a minimum optical path length of the probe.

14. The at least one non-transitory machine-readable storage medium of claim 13, wherein the imaging modality system is an optical coherence tomography (OCT) system, the at least one-machine readable storage medium further comprising instructions that when executed by the computing device, cause the computing device to:
move a reference mirror operably attached to the OCT system to the first position;
acquire a calibration image of the lumen while the mirror is disposed in the first position;
detect a position of a fixed pattern in the calibration image; and
adjust the position of the reference mirror based on the position of the fixed pattern in the calibration image.

15. The at least one non-transitory machine-readable storage medium of claim 13, wherein the imaging modality system is an optical coherence tomography (OCT) system, the at least one-machine readable storage medium further comprising instructions that when executed by the computing device, cause the computing device to:
move a reference mirror operably attached of the OCT system to a first position;
move the reference mirror from the first position; acquire a calibration image of the lumen while the reference mirror is moving from the first position;
detect a position of a fixed pattern in the calibration image; and
adjust the position of the reference mirror based on the position of the fixed pattern in the calibration image.

16. The at least one non-transitory machine-readable storage medium of claim 13, wherein the imaging modality system is an optical coherence tomography (OCT) system, the at least one-machine readable storage medium further comprising instructions that when executed by the computing device, cause the computing device to:
move a reference mirror operably attached of the OCT system to a first position;
initiate a pullback operation of the probe;
acquire a calibration image of the lumen while the probe is undergoing the pullback operation;
detect a position of a fixed pattern in the calibration image; and
adjust the position of the reference mirror based on the position of the fixed pattern in the calibration image.

* * * * *